United States Patent
Staker et al.

(10) Patent No.: US 9,488,823 B2
(45) Date of Patent: Nov. 8, 2016

(54) TECHNIQUES FOR SCANNED ILLUMINATION

(71) Applicant: Complete Genomics, Inc., Mountain View, CA (US)

(72) Inventors: Bryan P. Staker, Mountain View, CA (US); Craig E. Uhrich, Mountain View, CA (US)

(73) Assignee: Complete Genomics, Inc., Mountain View, CA (US)

( * ) Notice: Subject to any disclaimer, the term of this patent is extended or adjusted under 35 U.S.C. 154(b) by 599 days.

(21) Appl. No.: 13/908,964

(22) Filed: Jun. 3, 2013

(65) Prior Publication Data

US 2014/0152793 A1 Jun. 5, 2014

Related U.S. Application Data

(60) Provisional application No. 61/656,701, filed on Jun. 7, 2012, provisional application No. 61/656,774, filed on Jun. 7, 2012.

(51) Int. Cl.
*H04N 7/18* (2006.01)
*H04N 9/47* (2006.01)
(Continued)

(52) U.S. Cl.
CPC ......... *G02B 21/361* (2013.01); *G01N 21/6456* (2013.01); *G02B 21/365* (2013.01);
(Continued)

(58) Field of Classification Search
CPC ..... G02B 21/365; G02B 21/367; H04N 7/18
See application file for complete search history.

(56) References Cited

U.S. PATENT DOCUMENTS 3,706,848 A 12/1972 Rouet
4,174,159 A 11/1979 Kraft et al.
(Continued)

FOREIGN PATENT DOCUMENTS

| CN | 1461570 | 12/2003 |
|---|---|---|
| CN | 1700051 | 11/2005 |

(Continued)

OTHER PUBLICATIONS

International Search Report and Written Opinion for PCT Patent Application No. PCT/US2013/44250 mailed on Nov. 20, 2013, 12 pages.

(Continued)

*Primary Examiner* — Chikaodili E Anyikire
(74) *Attorney, Agent, or Firm* — Kilpatrick Townsend & Stockton LLP; Kenneth R. Allen

(57) ABSTRACT

Imaging systems are provided for high speed, high resolution imaging of biochemical materials. In an example embodiment, an imaging system comprises an objective lens component, a line generator, a digital camera, a positioning stage, and a scan mirror. The line generator generates a line of light that is scanned across a portion of a substrate that is mounted on the positioning stage. The positioning stage moves the substrate in a particular direction that is substantially normal to an optical axis of the objective lens component. The camera collects an image of the portion of the substrate through the objective lens component. The scan mirror moves in coordination with the positioning stage, while the line of light is being scanned across the portion of the substrate and the substrate is being moved in the particular direction, in order to keep the image still with respect to the camera while the image is being collected by the camera.

30 Claims, 13 Drawing Sheets

(51) Int. Cl.
*G02B 21/36* (2006.01)
*G06T 1/00* (2006.01)
*G01N 21/64* (2006.01)

(52) U.S. Cl.
CPC .............. *G06T1/0007* (2013.01); *H04N 7/18* (2013.01); *G01N 21/6452* (2013.01); *G06T 2207/10056* (2013.01); *G06T 2207/30072* (2013.01)

(56) References Cited

U.S. PATENT DOCUMENTS

| | | |
|---|---|---|
| 4,302,087 A | 11/1981 | Reinheimer et al. |
| 4,589,140 A | 5/1986 | Bishop et al. |
| 4,683,195 A | 7/1987 | Mullis et al. |
| 4,683,202 A | 7/1987 | Mullis et al. |
| 4,731,745 A | 3/1988 | Katagiri et al. |
| 4,800,159 A | 1/1989 | Mullis et al. |
| 4,883,750 A | 11/1989 | Whiteley |
| 4,965,188 A | 10/1990 | Mullis et al. |
| 5,210,015 A | 5/1993 | Gelfand et al. |
| 5,399,491 A | 3/1995 | Kacian et al. |
| 5,476,930 A | 12/1995 | Letsinger |
| 5,593,826 A | 1/1997 | Fung et al. |
| 5,854,033 A | 12/1998 | Lizardi |
| 5,871,921 A | 2/1999 | Landegren et al. |
| 5,990,479 A | 11/1999 | Weiss et al. |
| 6,174,670 B1 | 1/2001 | Wittwer et al. |
| 6,207,392 B1 | 3/2001 | Weiss et al. |
| 6,210,891 B1 | 4/2001 | Nyren et al. |
| 6,251,303 B1 | 6/2001 | Bawendi et al. |
| 6,287,824 B1 | 9/2001 | Lizardi et al. |
| 6,309,824 B1 | 10/2001 | Drmanac |
| 6,310,710 B1 | 10/2001 | Shahar et al. |
| 6,319,426 B1 | 11/2001 | Bawendi et al. |
| 6,322,901 B1 | 11/2001 | Bawendi et al. |
| 6,396,995 B1 | 5/2002 | Stuelpnagel et al. |
| 6,400,487 B1 | 6/2002 | Harris et al. |
| 6,401,267 B1 | 6/2002 | Drmanac |
| 6,423,551 B1 | 7/2002 | Weiss et al. |
| 6,426,513 B1 | 7/2002 | Bawendi et al. |
| 6,444,143 B2 | 9/2002 | Bawendi et al. |
| 6,544,732 B1 | 4/2003 | Chee et al. |
| 6,576,291 B2 | 6/2003 | Bawendi et al. |
| 6,753,906 B2 | 6/2004 | Shimada |
| 6,828,100 B1 | 12/2004 | Ronaghi |
| 6,833,246 B2 | 12/2004 | Balasubramanian |
| 6,864,052 B1 | 3/2005 | Drmanac |
| 6,891,610 B2 | 5/2005 | Nikoonahad et al. |
| 6,911,345 B2 | 6/2005 | Quake et al. |
| 7,070,927 B2 | 7/2006 | Drmanac |
| 7,335,898 B2 | 2/2008 | Donders et al. |
| 7,391,565 B2 | 6/2008 | Lauer |
| 7,476,831 B2 | 1/2009 | Juskaitis et al. |
| 7,586,682 B2 | 9/2009 | Ohtake et al. |
| 7,714,996 B2 | 5/2010 | Yan et al. |
| 7,782,528 B2 | 8/2010 | Fukuyama et al. |
| 7,929,857 B2 | 4/2011 | Baldwin et al. |
| 8,059,336 B2 | 11/2011 | Ptitsyn et al. |
| 8,175,452 B1 | 5/2012 | Staker et al. |
| 8,203,608 B2 | 6/2012 | Ziegenbein et al. |
| 8,428,454 B2 | 4/2013 | Staker et al. |
| 8,445,194 B2 | 5/2013 | Drmanac |
| 8,660,421 B2 | 2/2014 | Staker et al. |
| 2002/0045045 A1 | 4/2002 | Adams et al. |
| 2003/0017264 A1 | 1/2003 | Treadway et al. |
| 2004/0218263 A1 | 11/2004 | Brugal |
| 2005/0248837 A1 | 11/2005 | Sase et al. |
| 2005/0270640 A1 | 12/2005 | Miki |
| 2005/0280714 A1 | 12/2005 | Freeman |
| 2006/0011804 A1* | 1/2006 | Engelmann .......... G02B 21/008 250/201.3 |
| 2006/0024711 A1 | 2/2006 | Lapidus |
| 2007/0002434 A1 | 1/2007 | Juskaitis et al. |
| 2007/0087362 A1 | 4/2007 | Church et al. |
| 2007/0121107 A1 | 5/2007 | Tsai et al. |
| 2007/0147673 A1 | 6/2007 | Crandall |
| 2007/0207482 A1 | 9/2007 | Church et al. |
| 2009/0072171 A1 | 3/2009 | So et al. |
| 2009/0295963 A1 | 12/2009 | Bamford et al. |
| 2010/0090127 A1 | 4/2010 | Yekta et al. |
| 2010/0259605 A1 | 10/2010 | So et al. |
| 2011/0292200 A1 | 12/2011 | Van Dijk et al. |
| 2012/0099852 A1 | 4/2012 | Staker et al. |
| 2014/0152888 A1 | 6/2014 | Staker et al. |

FOREIGN PATENT DOCUMENTS

| | | |
|---|---|---|
| CN | 101764958 | 6/2010 |
| CN | 102246081 | 11/2011 |
| EP | 1808721 | 7/2007 |
| WO | 0184209 | 11/2001 |
| WO | 2010070553 | 6/2010 |
| WO | 2012/002893 A1 | 1/2012 |
| WO | 2012/058014 A2 | 5/2012 |
| WO | 2012/083438 A1 | 6/2012 |
| WO | 2013/184758 A2 | 12/2013 |
| WO | 2013/184762 A1 | 12/2013 |

OTHER PUBLICATIONS

International Search Report and Written Opinion for PCT Patent Application No. PCT/US2013/44258 mailed on Oct. 16, 2013, 11 pages.

International Search Report and Written Opinion of PCT Patent Application No. PCT/US2011/56211 mailed on Apr. 17, 2012, 11 pages.

International Preliminary Report on Patentability of PCT Patent Application No. PCT/US2011/56211 mailed on Feb. 18, 2014, 6 pages.

U.S. Appl. No. 13/907,801, Non-Final Office Action mailed on Jul. 7, 2016, 15 pages.

U.S. Appl. No. 13/907,801, Advisory Action mailed on Apr. 29, 2016, 4 pages.

Chinese Application No. 201380030227.4, Office Action mailed on Apr. 20, 2016, 10 pages. (2 pages of Translation, 8 pages of Original document).

U.S. Appl. No. 13/907,801, Final Office Action Mailed on Dec. 31, 2015, 16 pages.

U.S. Appl. No. 13/907,801, Non-Final Office Action mailed on Apr. 29, 2015, 15 pages.

European Application No. 13799902.5, Extended European Search Report mailed on Feb. 25, 2016, 7 pages.

European Application No. 13801133.3, Extended European Search Report mailed on Mar. 1, 2016, 6 pages.

CN Patent Application No. CN201380038130.8, Office Action mailed on Jul. 4, 2016, 8 pages.

\* cited by examiner

TECHNIQUES FOR SCANNED ILLUMINATION

TECHNICAL FIELD

The present invention is related generally to imaging systems and more particularly to high-speed, high resolution imaging of biochemical materials in planar arrays.

BACKGROUND

Obtaining useful data from images of biochemical experiments requires high spatial resolution, accuracy, and speed. Such images typically need to be captured at high enough magnification for individual experiments to be clearly resolved. At the same time, the images need to cover a large enough field of view for experiments to be correctly identified. For large-scale studies, the imaging and image processing must take place quickly enough in order to be commercially feasible.

Step-and-repeat imagers and time-delay integration (TDI) imagers are two broad types of imaging systems that can be used to image biochemical experiments. While for some applications these two types of systems may perform reasonably well, for other applications they suffer from some structural and functional disadvantages that adversely affect overall throughput. For example, applications involving large-scale biochemical experiment studies (e.g., such as massively parallel whole human genome sequencing) typically require overall throughput that is higher than what step-and-repeat and TDI imaging systems can currently deliver.

SUMMARY

According to the invention, imaging systems are provided for high speed, high resolution imaging of biochemical materials. In an example embodiment, an imaging system comprises an objective lens component, a line generator, a digital camera, a positioning stage, and a scan mirror. The line generator generates a line of light that is scanned across a portion of a substrate that is mounted on the positioning stage. The positioning stage moves the substrate in a particular direction that is substantially normal to an optical axis of the objective lens component. The camera, which employs circuitry that internally scans its electronic sensor and produces a serial readout of digital data representing a fraction of a two-dimensional image, collects an image of the portion of the substrate through the objective lens component. The scan mirror moves in coordination with the positioning stage, while the line of light is being scanned across the portion of the substrate and the substrate is being moved in the particular direction, in order to keep the image still with respect to the camera while the image is being collected by the camera.

The invention will be better understood by reference to the following detailed description with its accompanying drawings.

DETAILED DESCRIPTION

Figure 1A:
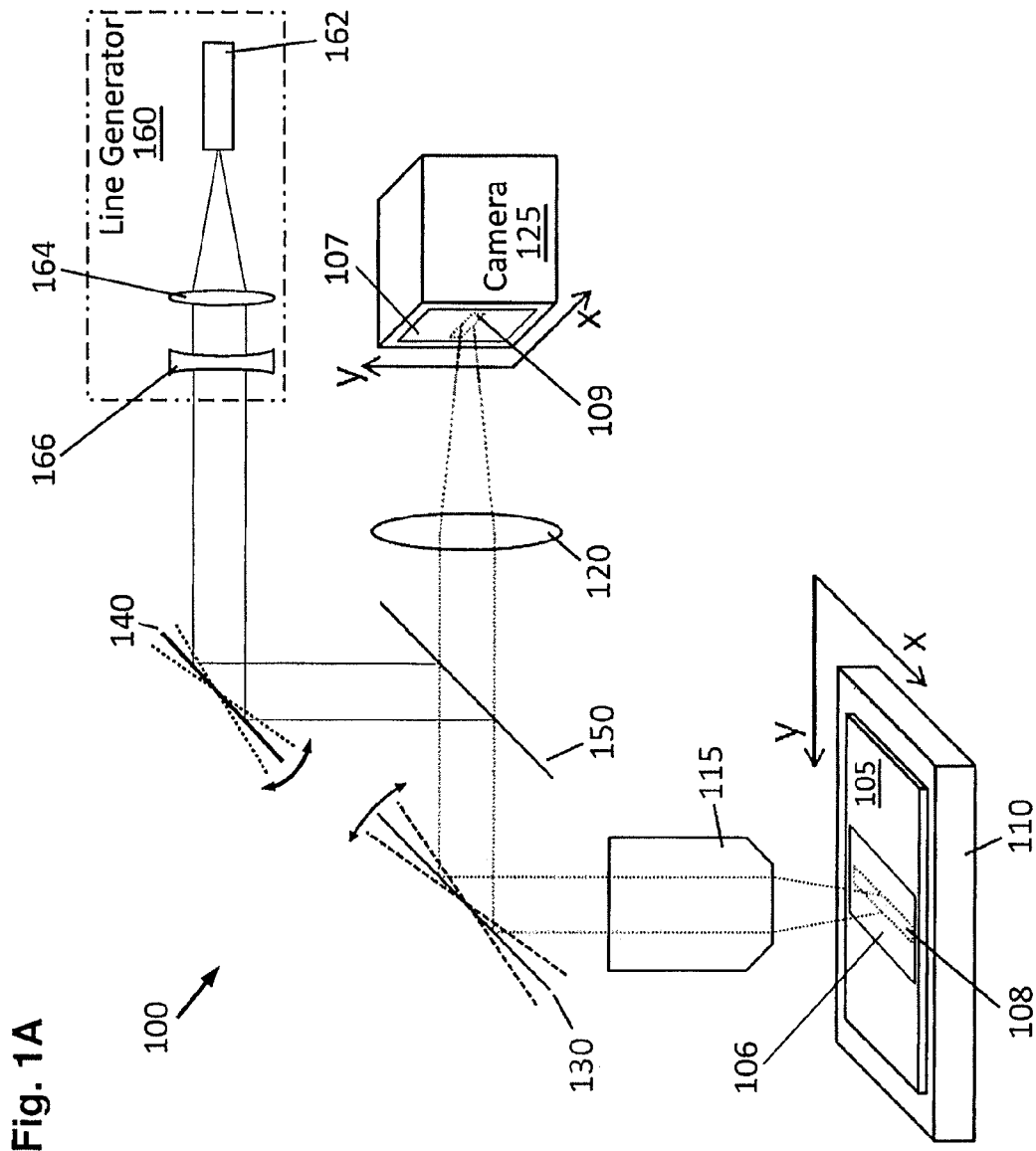
FIG. 1A is a block diagram illustrating some components in an example imaging system that employs scanned illumination according to one embodiment.

In the present disclosure, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The present disclosure describes embodiments of techniques for scanned illumination that may be used to conduct a variety of imaging and/or scanning operations such as, for example, operations used to observe and/or record biochemical experiments and other biochemical reactions.

Overview

In an example embodiment, a method for operating an imaging system comprises the steps of: collecting an image of a portion of a substrate with a digital camera in the imaging system, where the image spans multiple rows of pixels of a sensor element in the camera; while the camera is collecting the image of the portion of the substrate, performing steps comprising: scanning a line of light across the portion of the substrate thereby exposing first one or more rows of pixels spanned by the image while keeping in the dark second one or more rows of pixels spanned by the image, and reading out the first one or more rows of pixels while continuing to scan the line of light across the portion of the substrate thereby exposing the second one or more rows of pixels.

In an example embodiment, the method for operating the imaging system further comprises: moving the substrate under an objective lens component of the imaging system; and changing an angle of a scan mirror so that the image of the portion of the substrate that is acquired by the objective lens component is kept still with respect to the camera while the substrate is moving. In one aspect, reading out the first one or more rows of pixels is performed while the substrate is being moved in a direction that is normal to the optical axis of the objective lens component. In another aspect, changing the angle of the scan mirror is performed in coordination with scanning the line of light across the portion of the substrate. In another aspect, changing the angle of the scan mirror includes a first time interval during which the line of light is scanned across the portion of the substrate and a second time interval during which the scan mirror is returned to an initial position, where the method further comprises ceasing to scan the line of light across the portion of the substrate during the second time interval. In some aspects, the first time interval is greater than the second time interval.

In an example embodiment, the method for operating the imaging system further comprises scanning the line of light across the portion of the substrate by changing an angle of an illumination mirror to reflect light from a line generator onto the portion of the substrate. In one aspect, changing the angle of the illumination mirror comprises a servo mechanism tilting the illumination mirror. In another aspect, the method further comprises: moving the substrate under an objective lens component of the imaging system; and changing an angle of a scan mirror so that the image of the portion of the substrate, that is acquired by the objective lens component, is kept still with respect to the camera while the substrate is moving, where changing the angle of the scan mirror is performed in coordination with changing the angle of the illumination mirror.

In an example embodiment, the method for operating the imaging system further comprises keeping the first one or more rows of pixels dark between the steps of exposing the first one or more rows of pixels and reading out the first one or more rows of pixels.

In an example embodiment, the method for operating the imaging system comprises operating a camera that includes a split-readout sensor having at least two sections, and the steps of scanning the line of light and reading out are performed independently in each section of the sensor. For example, in one aspect the steps of scanning and reading out in one section are performed in parallel to the steps of scanning and reading out in another section, while in another aspect the steps of scanning and reading out in one section are performed in anti-parallel to the steps of scanning and reading out in another section.

In an example embodiment, the method for operating the imaging system comprises operating a camera that that is configured to operate in correlated double sampling mode. In some embodiments, the step of reading out is performed in rolling readout mode. In some embodiments, the line of light has a wavelength appropriate for fluorescence excitation while pixels in the camera are exposed by light having a wavelength corresponding to fluorescence emission.

In an example embodiment, while the camera is collecting the image of the portion of the substrate, the method for operating the imaging system further comprises reading out the second one or more rows of pixels while continuing to scan the line of light across the substrate thereby exposing third one or more rows of pixels spanned by the image, where the third one or more rows of pixels are different than the second one or more rows of pixels. In one aspect, the third one or more rows of pixels are different than the first one or more rows of pixels.

In an example embodiment, the method for operating the imaging system comprises operating one of a CMOS ("Complementary Metal-Oxide Semiconductor") camera and a non-CMOS camera operating in full-frame mode. In some embodiments, the camera is operating with readout efficiency in a range from 55% to 90%. In some embodiments, the camera is operating with readout efficiency of 90% or greater. In some embodiments, the camera is operating with a line rate in a range from 1,000 lines per second to 1,000,000 lines per second. In some embodiments, the camera has a number of camera pixels in a range from 100,000 pixels to 100 million pixels.

In an example embodiment, the method for operating the imaging system further comprises a positioning stage moving the substrate under an objective lens component of the imaging system with a velocity in a range from 100 µm/second to 1,000 mm/second and in a direction that is normal to an optical axis of the objective lens component.

In some embodiments, the method for operating the imaging system comprises imaging a substrate that comprises an array having target nucleic acids disposed thereon. In other embodiments, the method comprises imaging a substrate that comprises a multitude of distinct features that are targets for imaging.

In an example embodiment, an imaging system comprises an objective lens component, a line generator, a camera, a positioning stage, and a scan mirror. The line generator generates a line of light that is scanned across a portion of a substrate that is mounted (or otherwise placed) on the positioning stage. The positioning stage moves the substrate in a particular direction that is substantially normal to an optical axis of the objective lens component. The camera collects an image of the portion of the substrate through the objective lens component. The scan mirror moves in coordination with the positioning stage, while the line of light is being scanned across the portion of the substrate and the substrate is being moved in the particular direction, in order to keep the image still with respect to the camera while the image is being collected by the camera.

In an example embodiment, the imaging system further comprises an illumination mirror and a computer logic, where the image spans multiple rows of pixels in the camera, and where while the camera is collecting the image of the portion of the substrate: the illumination mirror scans the line of light across the portion of the substrate to expose first one or more rows of pixels spanned by the image while keeping in the dark second one or more rows of pixels spanned by the image; and the computer logic reads out the first one or more rows of pixels while the illumination mirror continues to scan the line of light across the portion of the substrate to expose the second one or more rows of pixels.

In an example embodiment, the imaging system further comprises an illumination mirror that scans the line of light from the line generator onto the portion of the substrate, where the scan mirror moves in coordination with the illumination mirror while the line of light is being scanned across the portion of the substrate and the substrate is being moved in the particular direction. In one aspect, the imaging system further comprises: a first servo mechanism that changes an angle of the illumination mirror to scan the line of light across the portion of the substrate; and a second servo mechanism that changes an angle of the scan mirror in coordination with changes to the angle of the illumination mirror. In one aspect, the second servo mechanism changes the angle of the scan mirror during a first time interval in which the line of light is scanned across the portion of the substrate; and the second servo mechanism returns the scan mirror to an initial position during a second time interval in which the line of light is not scanned across the portion of the substrate, where second time interval is shorter than the first time interval.

In an example embodiment, the imaging system further comprises a dichroic mirror that is operable at least to: (a) reflect the line of light from the illumination mirror onto the scan mirror in order to illuminate the portion of the substrate; and (b) pass to the camera light that is acquired by the objective lens component and is reflected by the scan mirror.

In an example embodiment, the imaging system comprises a camera that includes a split-readout sensor having at least two sections that can be exposed and read out independently of each other.

In some embodiments, the imaging system comprises a digital camera that is one of a CMOS camera and a non-CMOS camera operating in full-frame mode. In some embodiments, the camera operates with readout efficiency in a range from 55% to 90%. In some embodiments, the camera operates with readout efficiency of 90% or greater. In some embodiments, the camera operates with a line rate in a range from 1,000 lines per second to 1,000,000 lines per second. In some embodiments, the camera has a number of camera pixels in a range from 100,000 pixels to 100 million pixels.

In some embodiments, the imaging system comprises a positioning stage that moves the substrate with a velocity in a range from 100 μm/second to 1,000 mm/second.

In some embodiments, the imaging system is configured and operable to image a substrate that comprises an array having target nucleic acids disposed thereon. In other embodiments, the substrate comprises a multitude of distinct features that are targets for imaging.

In an example embodiment, a method of operating a digital camera comprises the steps of: (a) scanning a thin strip of light across an object to expose pixels in an image sensor of the digital camera row by row; and (b) reading out the pixels row by row in rolling readout mode after exposure in step (a). In some aspects, reading out the pixels takes longer than scanning the thin strip of light across the object. In some aspects, the pixels are kept dark between exposure and reading out. In some aspects, the digital camera comprises a split-readout sensor having at least two sections, where steps (a) and (b) are performed independently in each section of the sensor. For example, steps (a) and (b) in one section may be performed in parallel to steps (a) and (b) in another section; in another example, steps (a) and (b) in one section may be performed in anti-parallel to steps (a) and (b) in another section. In some aspects, the camera is operating in correlated double sampling mode. In some aspects, the thin strip of light has a wavelength appropriate for fluorescence excitation while pixels in the image sensor are exposed by light having a wavelength corresponding to fluorescence emission. In some aspects, the thin strip of light exposes two or more rows of pixels at a time.

It is noted that as used herein and in the appended claims, the singular forms "a," "an," and "the" may include plural referents unless the context clearly dictates otherwise. Thus, for example, reference to "an attachment site", unless the context dictates otherwise, may refer to multiple such attachment sites, and reference to "a method for sequence determination" may include reference to equivalent steps and methods that may be used by those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations, and methodologies which are described in the publication and which might be used in connection with the presently described invention.

Where a range of values is provided, it is understood that each intervening value, between the upper and lower limit of that range and any other stated or intervening value or sub-range in that stated range is encompassed within the invention. The upper and lower limits of such smaller ranges may independently be included in the smaller ranges, and are also encompassed within the invention, subject to any specifically excluded limit in the stated range. Where the stated range includes one or both of the limits, sub-ranges excluding either or both of those included limits are also included in the invention.

Selected Definitions

"Collecting an image" and grammatical equivalents thereof refer to a camera operation mode in which a set of camera pixels are activated and ready to collect and integrate a signal (e.g., such as light) of the image. For example, when activated, a camera pixel collects light if the pixel is exposed to light; if the camera pixel is not exposed to light (e.g., when the pixel is in darkness), then the pixel does not collect any light even though it is activated and ready to collect and integrate a light signal.

"Image space" refers to the area covered by the set of pixels in a camera, and "image space pixel" refers to a camera pixel.

"Logic" refers to a set of instructions which, when executed by one or more processors (e.g., CPUs) of one or more computing devices, are operable to perform one or more functionalities and/or to return data in the form of one or more results or of input data that is used by other logic elements and/or by elements that control the operation of mechanical devices (e.g., such as servos and the like). In various embodiments and implementations, any given logic may be implemented as one or more software components that are executable by one or more processors (e.g., CPUs), as one or more hardware components such as Application-Specific Integrated Circuits (ASICs) and/or Field-Programmable Gate Arrays (FPGAs), or as any combination of one or more software components and one or more hardware components. The software component(s) of any particular logic may be implemented, without limitation, as a stand-alone software application, as a client in a client-server system, as a server in a client-server system, as one or more software modules, as one or more libraries of functions, and as one or more static and/or dynamically-linked libraries. During execution, the instructions of any particular logic may be embodied as one or more computer processes, threads, fibers, and any other suitable run-time entities that can be instantiated in the hardware of one or more computing devices and can be allocated computing resources that may include, without limitation, memory, CPU time, storage space, and network bandwidth.

"Object space" refers to the area of an object (e.g., such as a substrate), and thus "object space pixel" refers to a unit of area on an object (e.g., such as a substrate). The size of object space pixels is typically determined by the size of the image space pixels (i.e., camera pixels) and the magnification that is applied when the camera is used to take images of the object space. The magnification is the ratio of the size of an image space pixel (i.e., a camera pixel) to the actual size of the object space area that corresponds to the image space pixel as observed by the camera. For example, a magnification of 16× allows a camera using 8 μm pixels to observe 500 nm object space pixels. In various embodiments, the size of an object space pixel may be between 100-1000 nm in width and 100-1000 nm in length; in a preferred aspect the size of an object space pixel may be 300 nm by 300 nm, more preferably 500 nm by 500 nm, even more preferably 620 nm by 620 nm. In some embodiments that use array chips, the size of an object space pixel is selected to be substantially the same as, or slightly bigger, than the size of an attachment site on an array chip, so that only a single discrete site will fit into an object space pixel. This ensures that, in operation, the intensity of the energy (e.g., light) emitted from an attachment site on the array chip can be recorded by a single camera pixel.

"Objective lens component" refers to an element or group of elements, in an imaging system, that comprises one or more lenses and is configured and operable to magnify an electromagnetic (e.g., such as optical) signal. In some embodiments, an objective lens component has a large numerical aperture (NA) (e.g., NA in a range between 0.95 and 1.5) and performs imaging via air immersion or liquid immersion (e.g., such as water, oil, or other immersion fluids). In various embodiments, an objective lens component may have a focal length in the range from 2 mm to 25 mm.

"Rolling readout mode" refers to a mode of operation in which rows of pixels in a camera sensor are consecutively read out one row at a time.

"Sequence determination" (also referred to as "sequencing") in reference to a target nucleic acid means determination of information relating to the sequence of nucleotides in the target nucleic acid. Such information may include the identification or determination of partial and/or full sequence information of the target nucleic acid. The sequence information may be determined with varying degrees of statistical reliability or confidence. In one aspect, the term "sequencing" includes the determination of the identity and ordering of a plurality of contiguous nucleotides in a target nucleic acid starting from different nucleotides in the target nucleic acid.

"Substrate" refers to an object having a multitude of distinct features that are targets for imaging. For example, in some embodiments a substrate comprises a non-planar structure with a surface, such as a bead or a well, to which target nucleic acids have been attached as the target features. In another example, in some embodiments a substrate comprises an array chip. "Array chip" (also referred to as "array", "microarray", or simply "chip") refers to a solid phase support having a surface, preferably but not exclusively a planar or substantially planar surface, that carries attachment sites to which target nucleic acids (e.g., such as macromolecules) have been attached as the target features. On an array chip, the attachment sites may be arranged in an ordered pattern or in random fashion, and are typically configured to have dimensions (e.g., length, width, and possibly depth or height) that are suitable for the attachment of target nucleic acids. An attachment site is thus spatially defined and is not overlapping with other sites; that is, the attachment sites are spatially discrete on the array chip. When attached to the attachment sites, the target nucleic acids may be covalently or non-covalently bound to the array chip. A "random array" (or "random microarray") refers to an array chip where the identities of the target nucleic acids (or of oligonucleotides or polynucleotides thereof) are not discernible, at least initially, from their location on the array chip but may be determined by a particular operation on the array, such as sequencing, hybridizing decoding probes, or the like. (See, for example, U.S. Pat. Nos. 6,396,995; 6,544,732; 6,401,267; and 7,070,927; WO publications WO 2006/073504 and 2005/082098; and US Pub Nos. 2007/0207482 and 2007/0087362. Also, some conventional microarray technology is reviewed in, for example, Schena, Ed. 2000, Microarrays: A Practical Approach, IRL Press, Oxford). The types and numbers of the target features of a substrate may vary in different implementations, operational contexts, and applications. For example, in various embodiments an array chip may have attached thereon a multitude of target nucleic acids in numbers that: (a) range between 1 million and 15 billion; (b) result in target nucleic acid occupancy of attachment sites in a range between 50% and 95% or greater; and/or (c) result in an average target nucleic acid density on the array chip in a range between 0.5 per $\mu m^2$ and 10 per $\mu m^2$ or greater. Further, in some embodiments, a substrate may be disposed in fluidic devices such as flow slides or flow cells. A flow slide is typically open to the environment and the rate of flow of liquids across the substrate is determined mainly by gravity. A flow cell, on the other hand, typically encloses its substrate from the environment and offers a closed liquid path that is used by a pressure-driven system (e.g., comprising various types of pumps, valves, lines, and other fluidic connections) to move fluids in and out of the flow cell. In general, in different embodiments and implementations, a substrate can be embodied in various and different devices with various and different features that are targets for imaging; for this reason, the examples of substrates and target features thereof described in this paragraph are to be regarded in an illustrative rather than a restrictive sense.

"Target nucleic acid" means a nucleic acid from a gene, a regulatory element, genomic DNA, cDNA, RNAs (including mRNAs, rRNAs, siRNAs, miRNAs, and the like), and fragments thereof, that is the subject of sequencing, observation, and/or other study. A target nucleic acid may be a nucleic acid from a sample, or a secondary nucleic acid such as a product of amplification and/or replication reaction(s). An example of such product is a macromolecule. "Macromolecule" used in relation to a nucleic acid means a nucleic acid having a measurable three dimensional structure, including linear nucleic acid molecules comprising secondary structures (e.g., amplicons), branched nucleic acid molecules, and multiple separate copies of individual sequences with interacting structural elements, e.g., complementary sequences, palindromes, or other sequence inserts that cause three-dimensional structural elements in the nucleic acid.

Imaging Systems for Scanning Moving Targets

In some embodiments, the imaging systems described herein are configured to scan a continuously moving target (e.g., such as a substrate) by using fast cameras that do not move the image through the camera. For example, in some embodiments imaging systems for DNA sequencing can be configured with CMOS cameras or scientific CMOS (sCMOS) cameras. Since full-frame cameras, unlike CCD-array cameras, cannot operate in TDI mode, the consequence of this operational limitation is that an image must not move with respect to the full-frame camera's sensor array during acquisition. The imaging systems described herein address this operational limitation at least in part by providing a scan mirror (and/or another optical device) that can hold the image still on the camera while a positioning stage is moving a substrate (e.g., an array chip) under an objective lens component. In this manner, the imaging systems described herein overcome the operational limitation of full-frame cameras (e.g., such as CMOS cameras) while attaining the advantages of these cameras' high speed, high resolution, and low cost. Examples of such imaging systems are described in U.S. Provisional Patent Application No. 61/656,701, titled "IMAGING SYSTEMS WITH MOVABLE SCAN MIRRORS" and filed on the same day herewith, the entire contents of which are hereby incorporated by reference as if fully set forth herein.

The imaging systems described herein preserve the use of mechanically desirable continuous stage motion, but freeze the image of a substrate with respect to a camera's sensor array during image acquisition. In some embodiments, this is accomplished through the use of a lightweight, servo-controlled, scan mirror that can be accelerated and decelerated much more easily and accurately than a heavier positioning stage. Devices for monitoring scan mirror performance and making small image position corrections on the fly may also be part of the imaging systems in some embodiments. As a result, an imaging system in accordance with the techniques describe herein can acquire 550 megapixels (or more) of image data per second while maintaining about 50 nm alignment accuracy. Coupled in a sequencing machine with suitable biochemical reaction subsystem, such imaging system allows for very high sequencing throughput such as, for example, sequencing of about 100 human genome equivalents of data per day.

In some embodiments, the imaging system is a fluorescence-based system that comprises an objective lens component, one or more cameras, a movable positioning stage, and preferably, but not exclusively, a tube lens component. In these embodiments the imaging system is configured and operable to take images of entire substrates (e.g., such as array chips) or of portions thereof, where the substrate is mounted or otherwise placed on the positioning stage and is in motion while the images are being taken by the camera(s). According to the techniques described herein, such imaging system allows the use of a really fast camera (e.g., such as a CMOS camera) to acquire images of the moving substrate. To facilitate this mode of system operation, the techniques described herein provide for a movable (i.e., tiltable) scan mirror that is disposed in the optical path between the objective lens component and the camera(s). This arrangement of components is in contrast to conventional imaging systems, which generally employ objective lenses and a camera that are perfectly aligned along the optical path and therefore do not allow for movable components in the middle of that optical path because such movable components generate effects that are considered undesirable in conventional imaging systems.

It is worth noting that fluorescence-based imaging systems that are used for DNA sequencing typically employ very low light levels because fluorescence images are dim. Thus, the camera(s) and the optics in such imaging systems need to be as efficient as possible in order to keep image acquisition time to a minimum. Further, illumination intensity must remain below the point where it can damage the target nucleic acids that are being sequenced. These factors are some of the actors that need to be taken into account when designing fluorescence imaging systems for imaging of moving target nucleic acids.

Fast Cameras and Imaging of Moving Targets

In some embodiments, the imaging systems described herein are configured to use fast cameras in conjunction with a movable scan mirror in order to achieve continuous exposure of a still image while the substrate being imaged is moving. In some embodiments, the size (length and/or width) of a camera pixel is in a range from 5 µm to 10 µm, preferably but not exclusively in the range of 6-8 µm.

In various embodiments, the imaging systems described herein are configured to scan a continuously moving substrate (e.g., such as an array chip) by using fast cameras that do not move the image through the camera—e.g., such as non-TDI cameras and other, cameras (including TDI cameras) that operate in full-frame mode. CMOS cameras are an example class of such cameras. CMOS cameras typically use an active-pixel sensor (APS) that is an image sensor comprising of an integrated circuit containing an array of pixels, where each pixel includes a photodetector and an active amplifier. One example of a CMOS camera is the SciMOS 2051 model from Fairchild Imaging, Milpitas, Calif. The SciMOS 2051 is a fast camera that can capture 5.5 megapixel images at 100 frames per second with 286 MHz readout and less than 2 electrons typical read noise.

Preferably, but not exclusively, the high speed of a camera is defined by line rate, which is an operational characteristic of the camera that defines the number of pixel rows that can be read out from the camera in a unit of time. The line rate of a camera can be determined according to equation (1) below:

$$R_{line} = \frac{P_{readout-frequency}}{N_{pixels-per-line}} \quad (1)$$

where "$R_{line}$" is the line rate of the camera, "$P_{readout-frequency}$" is the pixel readout frequency of the camera (e.g., the number of pixels that can be read out in a unit of time), and "$N_{pixels-per-line}$" is the number of pixels in a sensor row of the camera. For example, a camera that has 286 MHz readout frequency and 2560 pixels per array sensor row, would have a line rate of $R_{line}$=286 MHz/2560≈$10^5$ lines per second.

Alternatively, a high-speed camera may be defined in terms of the number of pixels that the camera can expose in a unit of time. For example, the speed of the camera may be defined by the mathematical product of the number of pixels in the field of view and the frames per second that the camera can take. Thus, a camera with a field of view of 5.5 megapixels (e.g., a view of 2560 pixels by 2160 pixels) running at 100 frames per second (fps) would be able to expose 550 megapixels per second; thus, such camera is termed herein as a "550" megapixel digital camera. Examples of such cameras include, without limitation, CMOS, sCMOS, and similar cameras. In various embodiments, the imaging systems described herein may use cameras in the range from 10 megapixels to 2500 megapixels.

In various embodiments, the imaging systems are configured to image moving substrates in a scanning fashion. In such embodiments, a substrate is typically mounted (or otherwise placed) on a positioning stage that is coupled to one or more mechanisms (e.g., such as motors, actuators, etc.) that can continuously move the substrate under an objective lens component while a camera is taking images of the substrate (or of portions thereof). The positioning stage is configured and operable to move the substrate along a direction that is normal to the optical axis of the objective lens component. (It is noted that this is orthogonal to the operation of autofocus-types of mechanisms, which generally move an object and/or an entire objective along the optical axis of the objective.)

According to the techniques described herein, the motion of the stage is coordinated with the reverse back-scanning motion of a scan mirror so that an image of the substrate (or portion thereof) is held still (stable) on the camera for a period of time that provides sufficient exposure. In other words, while the stage is moving, a still image of the substrate mounted thereon is being exposed to the camera. The image stabilization during the exposure period is provided by the motion (e.g., tilting) of a scan mirror in the optical path between the objective lens component and the camera. Thus, the scan mirror and the positioning stage are effectively coupled in a coordinated back-scanning operation in order to hold the image still/stable while the substrate being imaged is in continuous motion.

In an example embodiment of an imaging system, in operation the positioning stage is moving the substrate that is mounted thereon while a computer system executes logic to read one or more rows of exposed pixels from the camera. At the same time, the same and/or different computer system executes logic to synchronize the timing of the scan mirror to the timing of the positioning stage so that the scan mirror back-scans and keeps still another image on the camera thereby exposing another set of one or more rows of camera pixels.

In such mode of operation, the velocity of the positioning stage can be calculated according to equation (2) below:

$$V_{stage} = S_{pixel} * R_{line} * \eta \qquad (2)$$

where "$V_{stage}$" is the stage velocity, "$S_{pixel}$" is the size (e.g., length or width) of an object space pixel, "$R_{line}$" is the line rate of the camera (e.g., the rate at which rows of pixels are read out from the camera), and "$\eta$" is the efficiency of the overall readout from the camera (e.g., as expressed in a percentage or fraction of time that readouts can be extracted from the camera without compromising other on-going exposure). For example, in various embodiments, the size (e.g., length and/or width) of object space pixels can be in a range from 100 nm to 1000 nm, the camera line rate can be in a range from $10^3$ lines per second (Hz) to $10^6$ lines per second (Hz), and the efficiency of the overall readout from the camera can be in a range from 10% to 55%, from 55% to 90%, or greater than 90%. Thus, in various embodiments, the velocity of the positioning stage may be in a range from 0.1 mm per second to 1000 mm per second (or greater). In an example embodiment, the object space pixel is 620 nm, the camera line rate is $10^5$ lines per second (Hz), and the efficiency of the overall readout from the camera is 90%, which provide for a stage velocity of about 55.8 mm per second.

According to the techniques described herein, one or more computing devices and/or various logic thereof are configured and operable to control the coordinated motions of the scan mirror and the positioning stage. Thus, in some embodiments the positioning stage (and therefore the substrate mounted thereon) can be configured to move with constant velocity, in which case the back-scan motion of the scan mirror will also be at a suitable constant velocity. In other embodiments, the positioning stage can be configured to move with non-constant velocity, in which case the back-scan motion of the scan mirror will also be at a suitable non-constant constant velocity.

In various embodiments, various mechanisms may be used to facilitate the motion of the positioning stage at a given desired velocity. Such mechanisms may comprise one or more components that cause motion (e.g., such as linear motors, lead screws, screw motors, speed screws, etc.) and one or more components (e.g., such as various types of bearings) that reduce friction. For example, some embodiments may provide a mechanism with air bearings to move the positioning stage. An air bearing is a thin film of pressurized air that provides very low friction interface (e.g., a bearing gap) between two surfaces. Thus, in these embodiments the bottom surface of the positioning stage is not in direct contact with another surface but is rather suspended over an air bearing gap, which is such that (although the air constantly escapes from the bearing gap) the applied air pressure between the faces of the bearing is enough to support the load of the positioning stage. Use of such air bearings in the imaging systems described herein allows for locking a still image onto the camera within an alignment tolerance of 10-20 nm. In another example, some embodiments may use metal bearings (e.g., such as ball bearings, cylinder bearings, cross-roller ball bearings, etc.) that have repeatability of several microns. Even though such embodiments typically have greater alignment tolerances (e.g., tolerances greater than 20 nm), lower velocity of the positioning stage, and/or may use multiple camera pixels per object space pixels, such embodiments may still be commercially viable in certain application contexts.

As the above equation (2) illustrates, the efficiency of the overall camera readout ("$\eta$") is one parameter that determines the overall throughput of the imaging system. According to the techniques described herein, a readout efficiency of $\eta$=90% (or greater) can be achieved by using scanned illumination.

Imaging Systems with Scanned Illumination

In some embodiments, a fast CMOS camera employs correlated double sampling to achieve low read noise, and rolling readout mode to enhance throughput. The technical details associated with these operating modes, when combined with an imaging system that scans a moving target object, present some constraints on image acquisition techniques. For example, in rolling readout mode, a camera can start image acquisition immediately after finishing a readout operation. Thus, in order to keep the camera at maximum capacity and/or efficiency, it is preferable to maximize the fraction of time that image data is readout from the camera. However, in an imaging system that uses a scan mirror to image moving targets, the scan mirror needs to come back to its initial position, and during such "fly-back" time the image projected onto the camera is not stable.

In order to address this issue, the techniques described herein provide for using scanned illumination that maximizes the fraction of time that image data can be read out from the camera sensor. For example, in some embodiments an imaging system comprises a light generator and an angularly movable illumination mirror, where the line generator generates a line (e.g., such as thin strip) of light and the illumination mirror scans the line of light onto the moving target (e.g., a substrate such as an array chip) along the same axis in which the target is moving. During the "stable" image time (e.g., when the scan mirror holds the image still with respect to the camera), the line of light is scanned across the moving target to expose one or more rows of pixels that are ahead of those row(s) of pixels that have just have been exposed. This allows the imaging system to continuously read out rows of pixels just after those pixels have been exposed, thereby maximizing the camera capacity and efficiency. After the stable time is up, during the fly-back time interval when the scan mirror is returned to its initial position, the line of light is "turned off" (e.g., by a switch or by a designed aperture) thereby preventing the camera pixels from being exposed to an unstable image. In other words, as long as the line of line light goes at least a little faster than the row(s) of pixels being read out and as long as the exposure time is sufficient to acquire a still (and/or resolvable) image, image data can be read out from the camera almost 90%-95% of the time (or even up to 100% of the time if the motions and timings of the scan mirror and the illumination mirror are precisely synchronized). For example, if the scan mirror holds an image still on the camera during at least 90% of the scan mirror cycle (e.g., when the scan mirror fly-back time is less than 10% of the cycle), then this technique of using scanned illumination allows the camera to operate with at least η=90% overall readout efficiency.

Example Scanning Imaging System with Scanned Illumination

FIG. 1A is a diagram of a scanning fluorescence imaging system 100 according to an example embodiment. The imaging system of FIG. 1A illuminates a portion of a substrate (e.g., such as an array chip) by scanning a line of light across the substrate while an image of the portion of the substrate is temporarily fixed on the sensor of a camera as the substrate is being moved under a microscope objective lens component.

In the embodiment illustrated in FIG. 1A, array chip 105 carries target nucleic acids such as, for example, DNA macromolecules. Positioning stage 110 moves array chip 105 with respect to objective lens component 115 in the y-direction. Positioning stage 110 is a high-precision, computer-controlled, air-bearing stage. Objective lens component 115 is an off-the-shelf objective. In some embodiments, the objective lens component may be a custom-designed, multi-element optical component. Further, in some embodiments water immersion may be used to increase the numerical aperture (NA) of the objective lens component.

Objective lens component 115 and tube lens component 120 project an image of a portion of array chip 105 onto the sensor array of camera 125. Tube lens component 120 is an element or group of elements that comprises one or more tube lenses that function as a second magnification objective. Camera 125 is a fast CMOS camera that preferably, but not exclusively, operates in full-frame mode and employs a sensor array characterized by low read noise, high resolution, and high imaging speed.

In the embodiment illustrated in FIG. 1A, scan mirror 130 is a lightweight mirror that is tilted by a servo rotation mechanism (not shown) in a range of angular motion. As scan mirror 130 tilts back and forth between an initial and an end position, the area within the field of view 106 of objective lens component 115 is imaged onto camera 125 as image 107. When the motion of scan mirror 130 is coordinated with the motion of positioning stage 110, a fixed area (e.g., the field of view 106) on array chip 105 is imaged by the camera while the stage is moving. The rotation of scan mirror 130 (e.g., around an axis perpendicular to the plane of FIG. 1A) has the effect of scanning an image in the y-direction shown in the figure. This result is obtained because tilt in the collimated section of imaging system 100, in which scan mirror 130 is placed, corresponds to lateral translation at the focal plane of camera 125.

The illumination for fluorescence imaging is provided by line generator 160 in the form of a line of illumination light 108. The line of light 108 is directed to and reflected by illumination mirror 140, which is placed in an optical path between line generator 160 and dichroic beam splitter 150. In various embodiments, the line generator can emit light of various wavelengths that are compatible with various fluorophores that can be used in sequencing such as, for example, light of wavelength in a range from 400 nm to 800 nm. In FIG. 1A, line generator 160 comprises light source 162 (e.g., such as one or more lasers or other source of illumination), one or more collimating lenses 164, and one or more negative cylindrical lenses 166. Collimating lens 164 transforms the light emitted from light source 162 into a parallel beam of light, and negative cylindrical lens 166 focuses the parallel beam into a line of light. In various embodiments, the line of light generated in this manner is configured to have a length and/or width that correspond, after magnification, to the length and/or width of one or more rows of camera pixels. For example, with respect to the embodiment of FIG. 1A, the length and width of the line of illumination light 108 is such that the corresponding line of exposure light 109 spans one or more rows of pixels in the sensor of camera 125.

Illumination mirror 140 is a lightweight mirror that is tilted by a servo rotation mechanism (not shown) in a range of angular motion. As illumination mirror 140 tilts back and forth between an initial and an end position, the line of illumination light 108 generated by line generator 160 is reflected by the illumination mirror to dichroic beam splitter 150 and then to scan mirror 130, which in turn reflects it onto array chip 105 through objective lens component 115. Dichroic beam splitter 150 reflects at illumination wavelengths but transmits at fluorescence emission wavelengths; thus, beam splitter 150 reflects to scan mirror 130 the line of illumination light 108, and transmits to camera 125 the line of florescent exposure light 109. It is noted that in an imaging system that interrogates more than one type of fluorescent marker at a time, multiple illumination sources (e.g., such as multiple lasers each emitting a separate spectrum of light) and dichroic beam splitters may be used.

Illumination mirror 140 is positioned in the optical path of the line of illumination light 108 in a manner that allows the angular motion of the illumination mirror to effectively move the line of light across array chip 105 in the same direction (e.g., y-direction) in which positioning stage 110 is moving array chip 105. Since the motion of illumination mirror 140 is synchronized and/or coordinated with the motions of scan mirror 130 and positioning stage 110, the motion of the illumination mirror causes the line of illumination light 108 to be effectively moved, or scanned, across the portion of array chip 105 that is within the field of view 106 of objective lens component 115.

Since the motion of scan mirror 130 is coordinated with the motion of positioning stage 110, a fixed area covered by the field of view 106 on array chip 105 is imaged by camera 125 while the stage is moving (e.g., the image 107 projected onto the camera is stable). Rotating scan mirror 130 around an axis perpendicular to the plane of FIG. 1A has the effects of: (1) scanning the line of illumination light 108 onto array chip 105 in the y-direction (which is performed in coordination with the motion of illumination mirror 140), and (2) scanning an image 107 of a portion of array chip 105 also in the y-direction.

In operation, camera 125 collects image 107 of the area within the field of view 106 of objective lens component 115. (It is noted that in some embodiments the camera may be operating in rolling readout mode, while in other embodiments it may be operating in full-frame mode). The image 107 collected by camera 125 spans multiple rows of camera pixels (such image is also referred to herein as a "two-dimensional" image). Since the line of light 108 illuminates only a small line of a portion of array chip 105 at a time, at any one time the corresponding line of exposure light 109 only exposes one or a few rows of pixels spanned by image 107 while keeping in the dark other row(s) of pixels spanned by the image. (It is noted that such "in-the-dark" pixels may be pixels that have not yet been exposed or may be pixels that have already been exposed but have not yet been read out.) The motions and timings of illumination mirror 140, scan mirror 130, and positioning stage 110 are coordinated and synchronized in such manner that the line of illumination light 108 is at least slightly ahead of those row(s) of pixels that are currently being read out from camera 125 by a computer logic (not shown) in imaging system 100. For example, the line of exposure light 109, which is emitted by target nucleic acids on array chip 105 in response to excitation by the line of illumination light 108, is exposing row(s) of pixels in camera 125 that are (at least slightly) ahead of other row(s) of pixels that are currently being read out by the computer logic operating the camera. In this manner, image data can be read out from the camera while other image data is being acquired by the camera sensor, thereby increasing the overall camera readout efficiency η.

In some embodiments an imaging system may comprise one or more tilt plates, which are positioned in the optical path between the scan mirror and the camera, and which can be used to make small corrections to image placement on the sensor array of the camera—e.g., by using one tilt plate for corrections in the x-direction of the image and one tilt plate for corrections in the y-direction of the image. A tilt plate can be made of glass approximately 2.5 cm in diameter and 3.5 mm thick. The plate can be mounted on a servo rotation mechanism for quick and precise movements. Using the x-direction as an example, when light passes through a tilt plate at non-normal incidence, its position is offset by an amount Δx given by equation (3) below:

$$\Delta x = t\sin\theta - \frac{t}{n} \frac{\cos\theta \sin\theta}{\sqrt{1 - \left(\frac{1}{n}\sin\theta\right)^2}} \quad (3)$$

where "t" is the thickness of the plate, "n" is its index of refraction, and "θ" is the angle of incidence. For a glass plate (n=1.5) of the dimensions given above, a five degree tilt produces a lateral image offset of about 100 μm. A similar relationship holds for a tilt plate in the y-direction. Based on the above equation (3), information on image alignment with respect to the sensor array of the camera can be used to provide feedback signals that drive the x-direction tilt plate and/or the y-direction tilt plate. One source of such alignment information is the results of analyzing images acquired by the camera. Another source of alignment information in the y-direction can be obtained by monitoring the performance of the scan mirror by using one or more angle sensors that measure the tilt angle of the scan mirror precisely and quickly. In some embodiments, such image alignment information is sent to a computing device that executes the logic that controls the operation of the scan mirror, the chip positioning stage, the one or more tilt plates, and preferably (but not necessarily) the operation of the illumination source (s) and/or any illumination mirrors involved in illuminating the substrate being imaged.

In some operational contexts and applications, an imaging system can utilize the techniques for scanned illumination described herein without using a movable positioning stage and/or a movable scan mirror. For example, in one alternative embodiment an imaging system uses a movable illumination mirror to scan a line of illumination light across a stationary substrate and a camera operable to collect an image of a portion of the substrate. The camera operates in a mode (e.g., such as rolling readout mode or full-frame mode) that allows for exposing some row(s) of pixels while some other row(s) of pixels are being read out from the camera sensor. Since the substrate is stationary and is not moving during image acquisition, the imaging system does not need to employ a movable scan mirror to keep the image still on the camera. The motion of the illumination mirror and the operation of the computer logic, which reads out image data from the camera, are coordinated and synchronized in such manner that the line of exposure light (which is reflected from the substrate in response to the line of illumination light) is at least slightly ahead of those row(s) of pixels that are currently being read out from the camera by the computer logic. Such coordination and timing synchronization may depend on several factors that include, without limitation, the time necessary for sufficient exposure, the scan velocity of the line of illumination light across the substrate, and the like. Because such factors largely depend on the particular use of the imaging system, in this alternative embodiment the techniques for scanned illumination described herein can still be used to increase the overall readout efficiency η of the camera in some operational contexts, even though the imaging system does not employ a movable positional stage to image moving targets. Thus, embodiments (e.g., such as the embodiment illustrated in FIG. 1A) that use angularly movable illumination and scan mirrors in conjunction with linearly movable positioning stages are to be regarded in an illustrative rather than a restrictive sense.

Coordination and Synchronization in Scanning Operations

In some embodiments, an imaging system uses a movable illumination mirror to scan a line of light across a substrate (e.g., such an array chip) while a movable scan mirror temporarily fixes an image of the portion of the substrate on a camera as a positioning stage is moving the substrate under a microscope objective lens component. The motion of the illumination mirror is coordinated with the motions of the scan mirror and the positioning stage in a manner that allows the motion of the illumination mirror to cause the line of illumination light to be effectively moved, or scanned, across the portion of the substrate that is within the field of view of the objective lens component.

In an example embodiment, one or more computing devices in the imaging system execute computer logic that is configured and operable to synchronize the timing of the operations that read out image data from exposed row(s) of camera pixels with the motions of the illumination mirror, the scan mirror, and the positioning stage on which a target substrate is mounted. In operation, as a line of light reflected by the moving illumination mirror is scanned by the moving scan mirror across the substrate, the positioning stage is moving the substrate mounted thereon while a computing device executes readout logic to read one or more rows of exposed pixels from the camera. At the same time, the same and/or different computing device executes coordination logic that receives input data from the system elements that move the illumination mirror, the scan mirror, and the positioning stage, where examples of such input data include, without limitation, data specifying the current tilt angle of the illumination mirror, data specifying the current tilt angle of the scan mirror, and data specifying the position and velocity of the positioning stage. The coordination logic then uses the input data to determine whether any corrections are necessary in the motions and the timings of the illumination mirror, the scan mirror, and the positioning stage, and if so sends any necessary correction terms to the system elements that facilitate such motions.

In this manner, the coordination logic synchronizes the operation of the illumination mirror, the scan mirror, the positioning stage, and the readout logic. The result of this synchronization is that the scan mirror keeps the image of the substrate (or portion thereof) still with respect to the camera while the illumination light is scanned across the substrate, while at the same time the readout logic extracts image data from row(s) of pixels that have already been exposed. In some embodiments, as long as the coordination logic ensures that the line of exposure light is ahead of the row(s) of pixels currently being read out, the illumination mirror and the scan mirror do not necessarily need to operate with tolerances as strict as the tolerances required for the scan mirror to keep the image still on the camera. In other embodiments (e.g., that require extremely high image system throughput), the timing between readout logic, the illumination mirror, and the scan mirror may be synchronized within very strict tolerances in order to ensure that image data can be read out from the camera all, or almost all, of the time. For example, in some DNA sequencing embodiments, the imaging systems need to lock the image acquired by the camera with a precision of 10-15 nm, which requires a high degree of synchronization between the respective timings of the illumination mirror, the scan minor, the positioning stage, and the readout logic.

To maximize the fraction of time during which image data can be extracted from the camera, in some embodiments the illumination mirror, the scan mirror, and the positioning stage are coordinated in a manner that allows the exposure of one or more row(s) of pixels in the camera while other row(s) are kept in the dark; as soon as the exposure is completed, a computing device executes the readout logic to read out the exposed row(s) of pixels while at the same time the imaging system continues to scan the line of light across the portion of the substrate to expose other row(s) of pixels in the camera. Thus, when the line of exposure light is always just ahead of the row(s) of pixels that are being read out, and the camera is always exposing at least some rows of pixels even when image data is being read out from other rows of pixels, the overall readout efficiency η of the camera would be at maximum/optimum.

Because according to the techniques described herein the illumination is being scanned in the form of a line across the target substrate, charge is collected and integrated in a camera pixel only during the time interval in which the line of exposure light sweeps over that pixel; the rest of the time the pixel is in the dark and hence does not integrate any charge even though the pixel is ready to do so. Thus, as soon as the exposure is completed (e.g., the line of exposure light has just swept over the pixel), the charges accumulated by a row of pixels can be read out by executing the readout logic, which reads the pixels row-by-row in a rolling fashion.

Scan Mirror Fly-Back

In embodiments that use servo-controlled mirrors, the synchronization between the motions and timings of the illumination mirror and the scan mirror do not necessarily need to be within strict tolerance, but the illumination mirror needs to complete its cycle (e.g., from its initial position to its end position) within the "stable" time interval of the scan mirror (e.g., the time interval during which the scan mirror holds the image still with respect to the camera). For example, in an imaging system that uses a scan mirror to image moving targets, the scan mirror needs to come back to its initial position, and during such "fly-back" time interval the image projected onto the camera is not stable; thus, if such imaging system employs scanned illumination as described herein, any component that facilitates the scanning of the illumination (e.g., such as a servo-controlled illumination mirror) needs to complete its cycles prior to any fly-back time intervals. For example, in imaging systems that use non-TDI-operating cameras to image moving targets, the implication of the fly-back time interval is that camera pixels should not be exposed during the scan mirror fly-back intervals but already-exposed pixels can be read out.

Figure 1B:
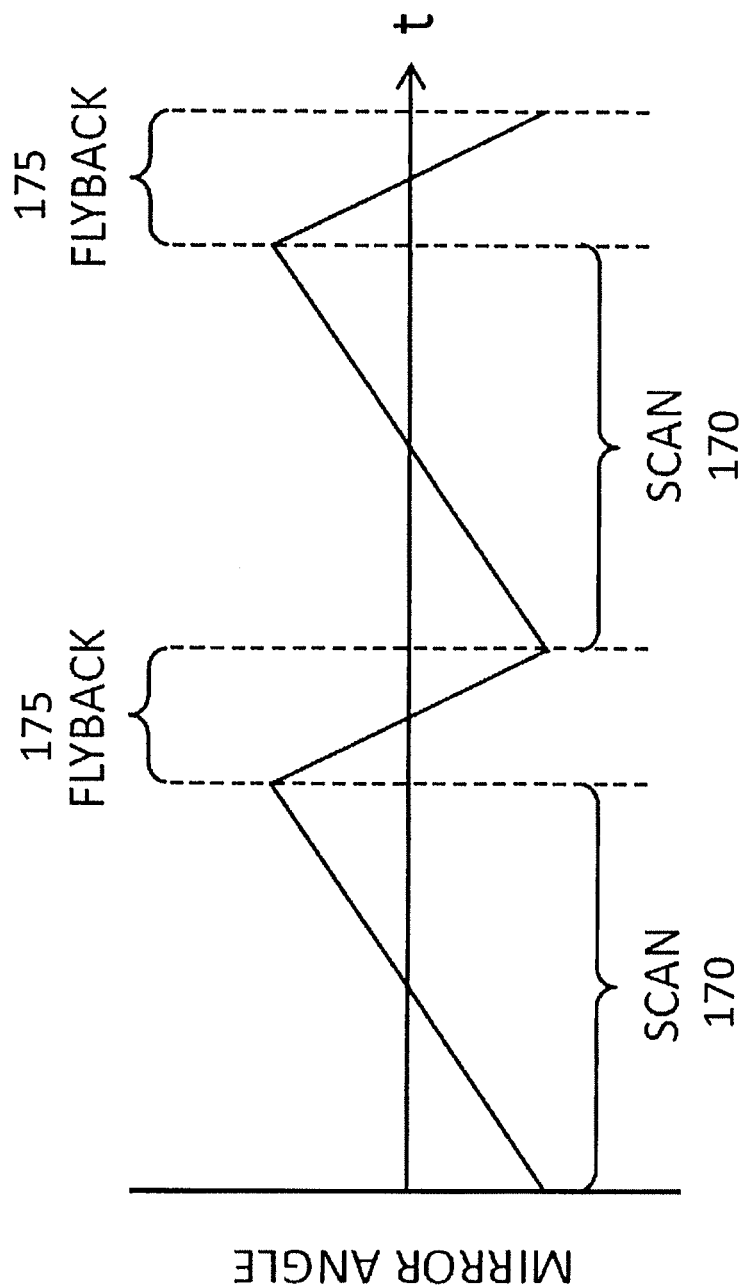
FIG. 1B is a diagram of scan mirror angle timing according to an example embodiment.

FIG. 1B illustrates a diagram of scan mirror angle timing according to an example embodiment.

In FIG. 1B, the tilt angle of a scan mirror is plotted versus time, t. During the periods 170 (marked "SCAN") the mirror angle changes substantially linearly with time so that a camera can view a fixed area on a moving substrate. During the periods 175 (marked "FLYBACK") the scan mirror returns to its starting angle (e.g., in initial position) in preparation for a new scan. One consequence of this behavior is that images should not be acquired during the fly-back time intervals. However, while the sensor of the camera should not be exposed during the scan mirror fly-back, image data may be read out from the camera at any time.

In some DNA sequencing embodiments, image data is read out continuously from the camera for maximum data throughput (e.g., such as image conversion into digital data) since there is no reason to stop reading out data or slowing down throughput. However, in such embodiments the scan time interval, during which an image is collected by the camera, must still be long enough to build up adequate signal-to-noise ratios as fluorescence imaging light levels are typically very weak.

During the fly-back time intervals, the imaging system should cease imaging because the image being acquired is not stable. Thus, in various embodiments various mechanisms can be used to prevent image exposure to the camera during the fly-back time intervals. For example, in some embodiments an acousto-optic modulator (AOM) switch (or other type of fast switch) may be used to turn on and off the line generator that generates the line of illumination light that is reflected onto the substrate being imaged. In other embodiments, a suitable aperture can be placed in the optical path of the line of illumination light, where the line of illumination light is allowed to overscan but the aperture prevents the line of light from illuminating the substrate during the fly-back time intervals by blocking out the line of light outside of the field of view. In yet other embodiments, a suitable shutter can be placed in the optical path of the line of illumination light, where the shutter is kept open during exposure intervals and is closed during the scan mirror fly-back time intervals.

Figure 1C:
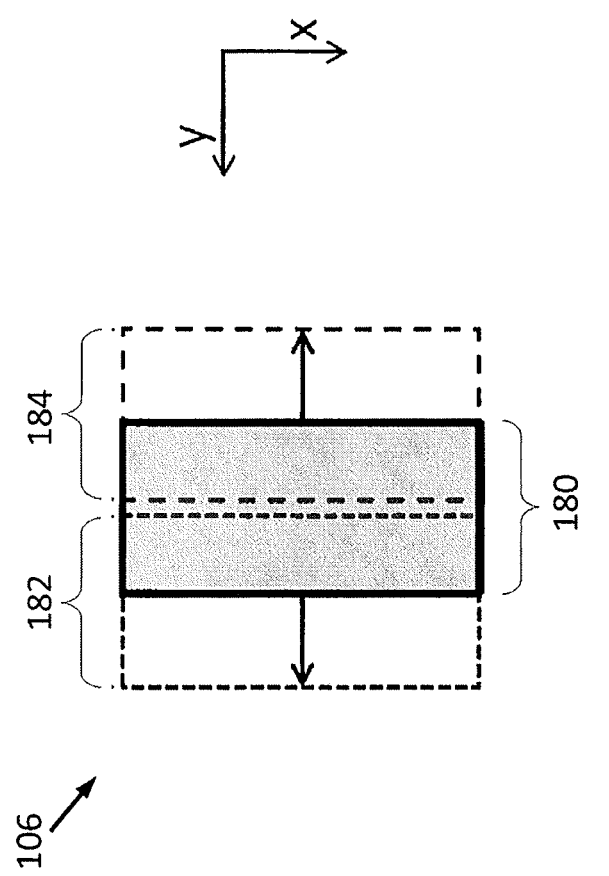
FIG. 1C is a diagram with example details of imaging areas within a microscope field of view according to one embodiment.

In this manner, the techniques for scanned illumination described herein can avoid any reduction in camera readout efficiency that may be caused by the fly-back time intervals of scan mirrors that are used in imaging systems to scan moving targets Example Scanning Operations FIG. 1C is a detail of object space areas within a field of view 106 of an objective lens component 115 according to the example embodiment of FIG. 1A. In FIG. 1C, shaded rectangle 180 represents the area within field of view 106 that is imaged on the sensor array of a camera when the scan mirror of the imaging system is in a mid-range position. Rectangles 184 and 182 (with dashed line borders) represent the area within field of view 106 that is imaged on the sensor array of the camera when the scan mirror is in its extreme initial and end positions, respectively.

In operation, the objective lens component is focused on a substrate (e.g., such as an array chip) that is steadily moving in the y-direction and the scan mirror rotates from its initial position to its end position. If the velocity of the substrate is the same as the velocity of the field of view 106 that is imaged on the camera, then the image of the substrate portion corresponding to the field of view does not move with respect to the camera, thereby allowing sufficient exposure onto the camera sensor.

With respect to FIG. 1C, however, the image is stationary with respect to the camera only during the time that the imaged object space area moves from the initial position indicated by rectangle 184 to the end position indicated by rectangle 182. When the scan mirror reaches its extreme end position, it must then fly-back to its initial position. The fly-back time interval can be configured to be only a small fraction of the scan mirror cycle, however, and consecutive imaged areas may be made contiguous or even overlap if necessary. For better efficiency, the amount of time spent by the scan mirror on each imaged area is made commensurate with the camera's frame rate, thereby allowing sufficient time to expose an image of each object space area onto the camera while at the same time allowing image data to be read out from the camera for other object space areas that have already been imaged and are out of the field of view.

To break the imaging problem into manageable chunks, in some array chip embodiments the attachment sites of an array chip are divided into micron-to-millimeter sized fields. (For example, in various aspects a typical field may be of a size in the ranges of 320-1600 μm by 320-1600 μm, 500-600 μm by 500-600 μm, or even 1.6 mm by 700 μm.) A typical array chip may be divided into hundreds or thousands of fields that are arranged in a rectangular pattern of rows and columns. (For example, the rows and columns of fields may include track regions that are aligned substantially along a horizontal dimension and a vertical dimension, respectively.)

In such embodiments with fields of attachment sites, the techniques described herein provide for scanning and imaging the array chip portion-by-portion, where each portion is a column that spans one or more fields in length and one or more fields in width. In one example, an imaging system images an array chip in a scanning fashion with scanned illumination (as described herein) while the positioning stage is moving the array chip along the y-direction in a plane and/or axis that is substantially normal to the optical axis of the objective lens component. In this example, the imaging system ceases imaging when the end of the column of field(s) being imaged is reached in order to allow the positioning stage to return the array chip and to position it for imaging of the next column of field(s). In another example, an imaging system images an array chip in a scanning fashion (as described herein) while the positioning stage is moving the array chip backward and forward in a serpentine fashion (e.g., along a y-axis) in a plane that is substantially normal to the optical axis of the objective lens component. In this example, the imaging system images a column of field(s) while the positioning stage is moving the array chip in one direction and then images the next/adjacent column of field(s) while the positioning stage is moving/returning the array chip in the opposite direction; in other words, the imaging system images the array chip by effectively traversing the columns of fields in a continuous serpentine fashion.

Rolling Readout Mode and Rolling Exposure Mode

Figure 2:
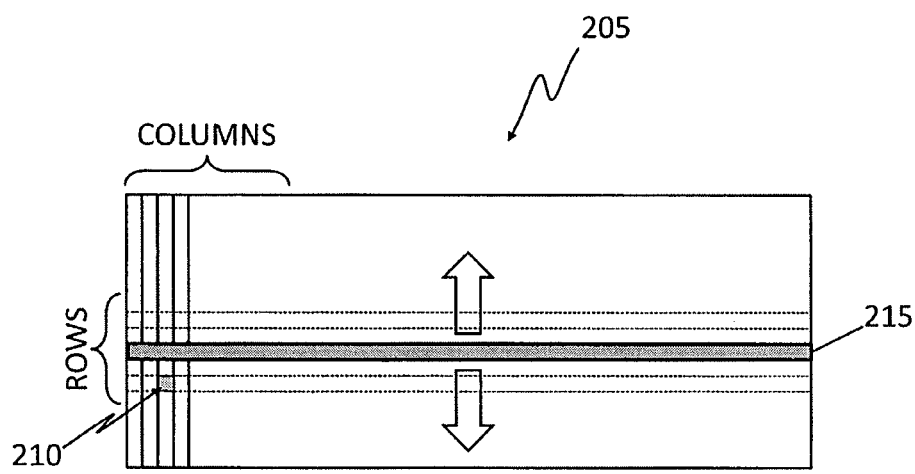
FIG. 2 is a diagram of example operations in rolling readout mode according to one embodiment.

In some embodiments, imaging systems use CMOS cameras that can operate in correlated double sampling mode to achieve low read noise. Further, the cameras in such systems may also operate in rolling readout mode to enhance throughput. FIG. 2 illustrates a diagram of example operations in rolling readout mode according to one embodiment.

FIG. 2 illustrates a few representative rows of pixels (e.g., pixel 210) in the image sensor 205 of a digital camera. (For illustration purposes, only a few columns of pixels have been depicted in FIG. 2; however, it is noted that columns of pixels extend along the entire width of sensor 205—that is, the sensor is a grid of rows and columns of pixels.) In various embodiments, the image sensor of a camera may include anywhere between 250 and 10,000 rows of pixels and anywhere between 400 and 10,000 columns of pixels, for a total number of pixels in a range from 100,000 to 100 million pixels.

In rolling readout mode, image data is read out from a camera sensor on a row-by-row basis. In other words, data from an entire row of pixels is read out simultaneously. As an example, image data from row 215 in FIG. 2 is read out at once. After that, data from an adjacent row of pixels is read out. According to the techniques described herein, rows are not readout randomly, but rather in a sweeping or "rolling" fashion up or down the sensor. For example, the two arrows in FIG. 2 suggest two possibilities: the next row of pixels read out after row 215 will be the adjacent row just above it, or the adjacent row just below it. Rolling readout mode can provide up to a factor of two increase in frame rate over global shutter or snapshot mode.

In some embodiments, the use of correlated double sampling to achieve low read noise means that image acquisition can begin immediately after readout. For example, pixels in the camera sensor can begin to accumulate light that contributes to image data immediately after data is read out. As long as no light falls on the camera sensor however, e.g., it is in the dark and is not exposed, then image noise does not build up. These operational details lead to a new exposure mode that takes advantage of correlated double sampling and rolling readout mode in an imaging system that has exposure dead time, e.g. such a fly-back time interval.

According to the techniques described herein, this new exposure mode is based on illuminating object space area (of whatever is to be imaged, e.g. such as a substrate) that corresponds to one, or just a few, rows of pixels in a camera sensor, where the illumination is scanned or "rolled" over the object space area. This exposure mode is referred to herein as "rolling exposure mode". Thus, in some embodiments an imaging system operates in both rolling exposure mode (in which a line of light is scanned across the substrate being imaged) and rolling readout mode (in which rows of pixels are read out one after the other shortly after exposure). A period of darkness between exposure and read operations does not increase image noise. The basic principles of this technique are shown in FIG. 3, which illustrates expose and read regions of a camera being operated in both rolling exposure mode and rolling readout mode.

Figure 3:
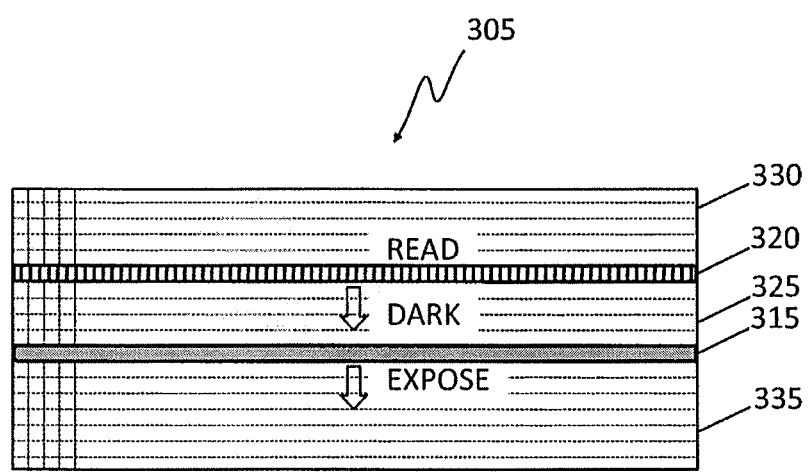
FIG. 3 is a diagram of example expose and readout regions.

FIG. 3 illustrates a few representative rows of pixels in camera sensor 305. (For illustration purposes, only a few columns of pixels have been depicted in FIG. 3; however, it is noted that columns of pixels extend along the entire width of sensor 305—that is, the sensor is a grid of rows and columns of pixels.) Shaded row 315 is currently being exposed—that is, the pixels in row 315 are recording image data. Hatched row 320 is being read out—that is, the image data in row 320 is being converted into electronic bits suitable for transmission to, and manipulation by, a computing device. Rows such as row 325, between row 315 and row 320, are dark; these rows have accumulated and integrated light signal during previous exposure, but have not yet been read out. No more light and no more noise is added in the darkness to rows such as row 325. The pixels in rows such as rows 330 and 335 are ready to collect image data (e.g., to accumulate and integrate light signal); with respect to the direction of the exposure and readout operations, such rows of pixels are located both behind the current readout row (e.g., such as row 320) and in front of the current exposure row (e.g., such as row 335).

Although FIG. 3 shows only one row 315 being exposed, in practice a few (e.g., one to about 10 or so) rows of pixels may be exposed simultaneously. The rows of pixels being exposed correspond to the line of illumination light that is scanned across the object space area being imaged (e.g., such a portion of a substrate). Thus, unlike traditional fluorescence microscopy in which the whole area visible through a microscope objective is illuminated at once, according to the techniques for scanned illumination described herein the illuminated object space area corresponds to just one or a few rows of pixels in the camera sensor. Further, the readout operation proceeds one row at a time in rolling readout mode as described above.

For example, with respect to FIG. 3, the line of illumination light is scanned across an object space area corresponding to an exposure area of the camera sensor that includes row 315 (as indicated by the "EXPOSE" arrow). The readout area of the camera sensor (as indicated by the "DARK" arrow) includes row 320 and follows behind the exposure area. In some embodiments, the exposure area and the readout area may "move" across the sensor at different speeds relative to each other.

Examples of Expose and Readout Timing

Figure 4:
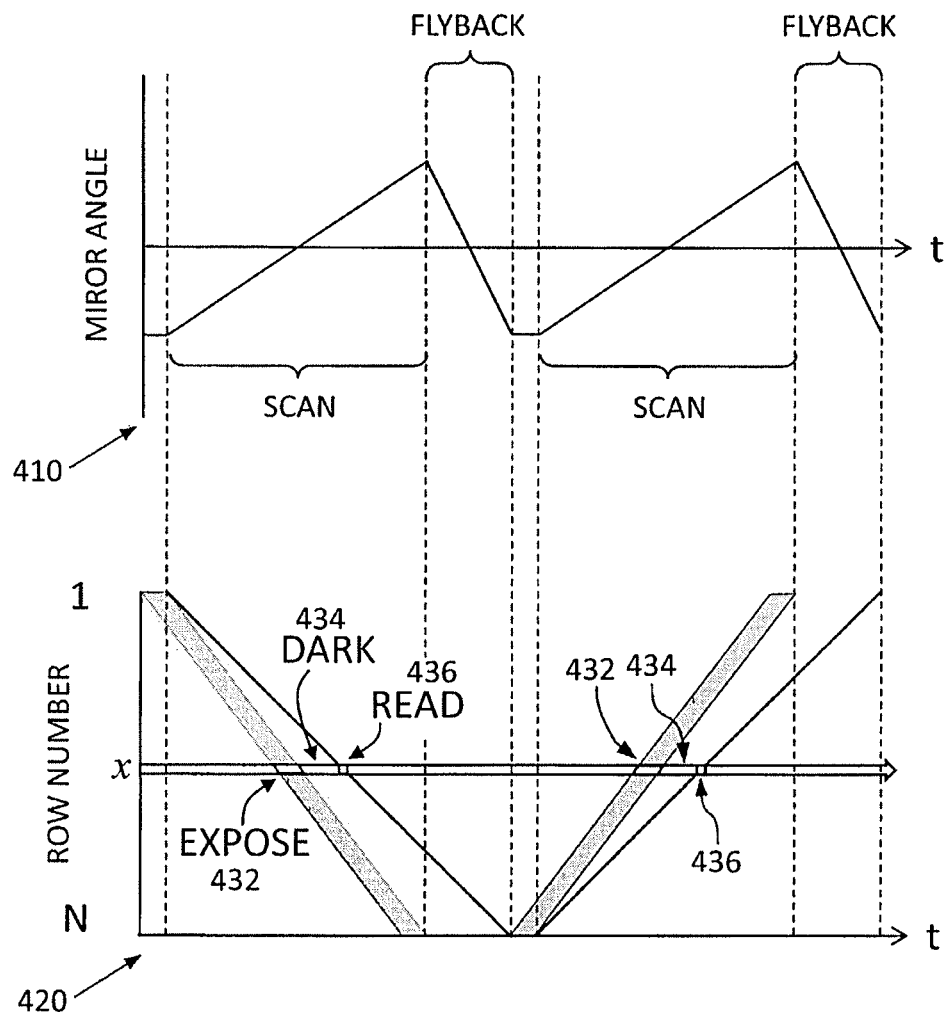
FIG. 4 is a diagram of mirror angle, expose timing, and readout timing according to an example embodiment.

FIG. 4 illustrates a diagram of scan mirror angle, expose timing, and readout timing according to an example embodiment.

Similarly to FIG. 1B, the upper diagram 410 in FIG. 4 shows a scan mirror angle plotted versus time, t. The lower diagram 420 in FIG. 4 shows a plot of exposed/read row numbers versus time, t. Rows of pixels (e.g., of a camera sensor) are numbered from "1" to "N", with the time sequence for row "x" expressly plotted out for illustration. Vertical slices (parallel to the dashed lines) of diagram 420 show which rows of pixels are being exposed or read during a particular time interval (e.g., such as a "SCAN" time interval or a "FLYBACK" time interval). Horizontal slices in diagram 420, e.g. as shown for row "x", show exposure, dark, and readout periods for a particular row.

As illustrated in FIG. 4, the tilt angle of a scan mirror (which holds an image still with respect to a camera sensor) is a linear function of time during "SCAN" intervals; the angle resets to a starting position during "FLYBACK" intervals. Exposure and readout of camera sensor rows sweep from one side (row "1") of the sensor to the other (row "N") and then back in the opposite direction (from row "AT" back to row "1"). While this may seem counterintuitive at first, it can be understood by remembering that the scan mirror "freezes" an image of a portion of a substrate (e.g., such as an array chip) on the camera sensor even though the substrate is moving in a direction that is normal to the objective lens component of the imaging system. Thus, the camera "sees" a still object that is illuminated by a moving line of light that covers an object space area corresponding to one (or a few) rows of camera pixels at a time. The readout operation is taking place in rolling readout mode a few rows behind the exposed row(s) of pixels.

FIG. 4 illustrates that the time required to expose "N" rows of pixels is shorter than the time needed to read out the image data stored therein. Thus, the exposure operation takes up all of the available scan time, i.e. the time that an image is still with respect to the camera sensor. The readout operation, on the other hand, can take place substantially continuously (with the only exception being the small delay that occurs before the beginning of exposure time for a first row in any given scan.)

FIG. 4 illustrates the exposure period, the dark period, and the readout period for a single row. Using row "x" as an example, exposure to illumination lasts for the "EXPOSE" time period 432. (It is noted that in fluorescence imaging, an object is exposed at a fluorescence excitation wavelength while pixels detect light at a fluorescence emission wavelength.) A "DARK" time period 434 follows the exposure period 432. During the dark period 434, neither signal nor noise accumulates in the pixels of row "x". The pixels of row "x" are read out during the "READ" time period 436, which occurs after time period 434. The time period (e.g., the dark time period) between the exposure operation and the readout operation increases as the line of exposure light moves across the object because the exposure operation proceeds at a higher speed than the readout operation. As indicated in FIG. 4, the exposure period 432, the dark period 434, and the readout period 436 are repeated during the next scan mirror cycle as the sensor rows are exposed (for a new image) in the reverse direction (e.g., from row "N" back to row "1"), which can happen when the imaging system is configured to scan an object (e.g., such as substrate) by traversing the object in a serpentine fashion.

Split-Readout Camera Sensor

In some embodiments, an imaging system comprises a camera having a spilt-readout sensor. A split-readout sensor has at least two sections that can be exposed and read out independently of each other, where the exposure/readout operations in one section can be performed in parallel or in anti-parallel with respect the exposure/readout operations in the other section(s) of the sensor. According to the techniques for scanned illumination described herein, in such embodiments each section of the split-readout sensor is illuminated with a separate line of light. Separate lines of light can be generated in various ways. For example, a separate line generator can be used to generate a separate line of light for each separate sensor section, where polarization can be used to direct the lines of light onto different portions of the same substrate. In another example, various optical components (e.g., such as prisms, half-silvered mirror, etc.) can be used to split a beam of light from the same line generator into two or more separate lines of light.

Figure 5:
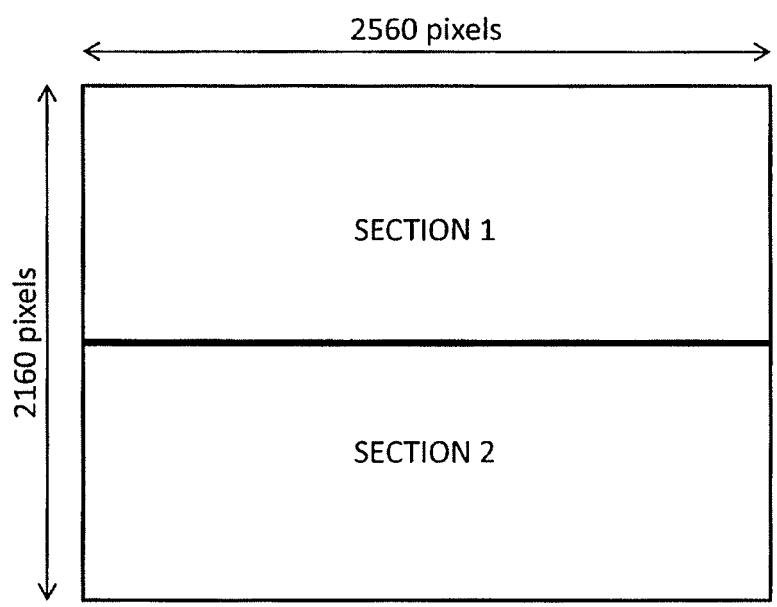
FIG. 5 is a diagram of an example split-readout camera sensor according to an example embodiment.

FIG. 5 illustrates a diagram of a split-readout camera sensor according to an example embodiment. In FIG. 5, a 2160 pixels by 2560 pixels sensor is split into "SECTION 1" and "SECTION 2". (The number of pixels shown in the sensor of FIG. 5 corresponds to the SciMOS 2051 camera of Fairchild Imaging, Milpitas, Calif., and is used as an example only. Other cameras may use split-readout sensors of different dimensions.) Each section of the sensor is read out independently of the other. Split-readout sensors lead to different ways of implementing the rolling exposure mode and the rolling readout mode described herein.

Figure 6A:
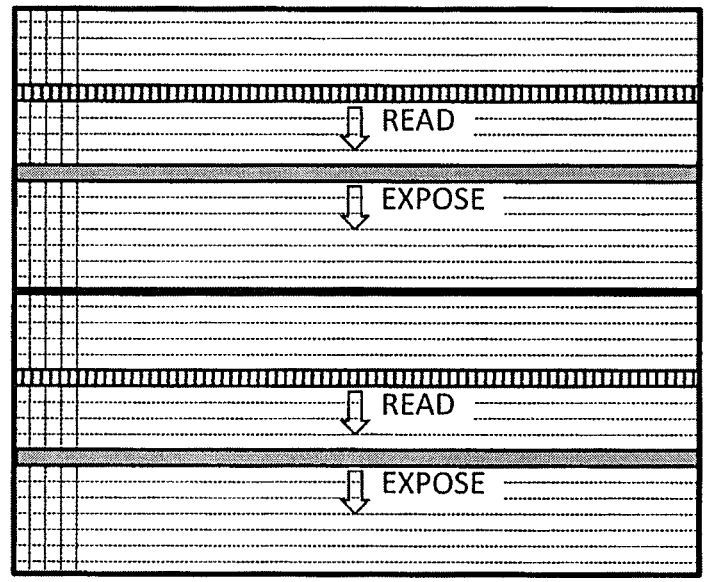
FIGS. 6A and 6B are diagrams of parallel operation of expose and readout regions in rolling readout mode according to an example embodiment.
Figure 6B:
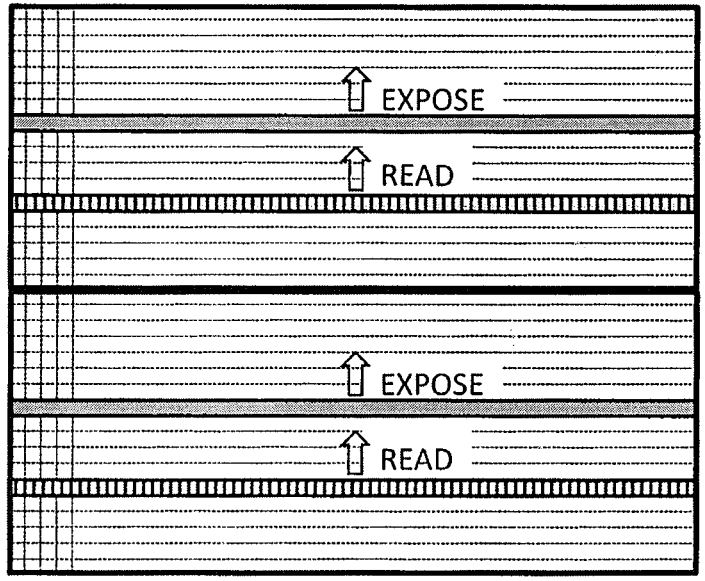
Figure 7A:
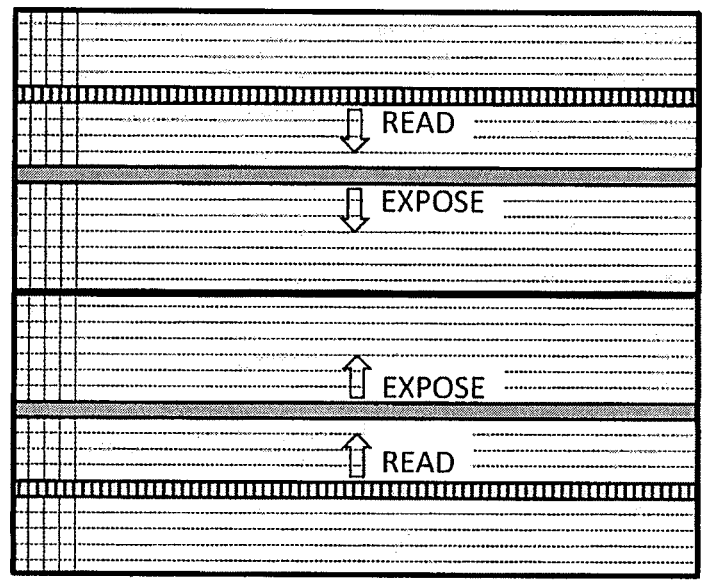
FIGS. 7A and 7B are a diagram of anti-parallel operation of expose and readout regions in rolling readout mode according to an example embodiment.
Figure 7B:
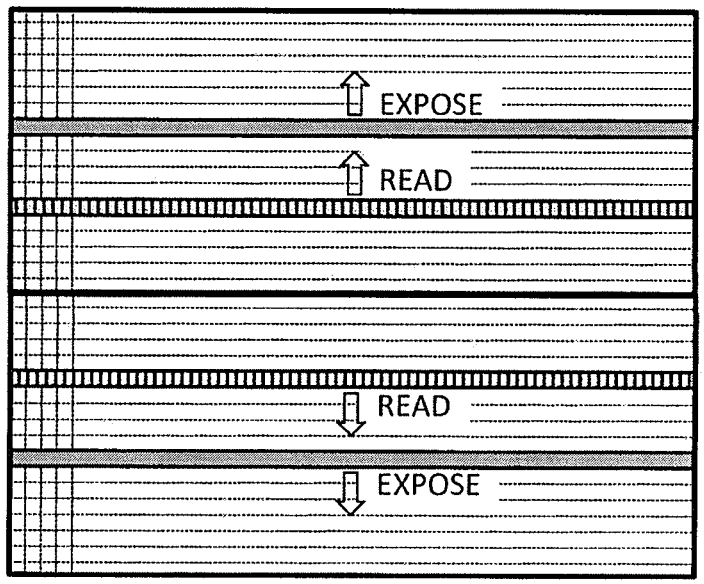

FIGS. 6A and 6B illustrate a diagram of parallel operation of exposure and readout regions according to an example embodiment that uses a split-readout camera sensor. FIGS. 7A and 7B illustrate a diagram of anti-parallel operation of exposure and readout regions according to an example embodiment that uses a split-readout camera sensor. Each of FIGS. 6A, 6B, 7A, and 7B illustrates a few representative rows of pixels in a camera sensor. For illustration purposes, only a few columns of pixels have been depicted in each of FIGS. 6A, 6B, 7A, and 7B; however, it is noted that columns of pixels extend along the entire width of the depicted sensor—that is, the sensor is a grid of rows and columns of pixels.

The sensor illustrated in FIGS. 6A and 6B is similar to the sensor illustrated in FIG. 3, except that the sensor of FIGS. 6A and 6B is a split-readout sensor having two sections. Pairs of exposure (marked "EXPOSE") and readout (marked "READ") regions, one pair for each section, move in the same direction in both sections of the sensor. For example, the pairs of exposure and readout regions move from top to bottom in both sections of the sensor in FIG. 6A and from bottom to top in both sections of the sensor in FIG. 6B. This mode of operation is referred to herein as "parallel" because the pairs of expose and readout regions of the sensor sections move in the same direction.

The sensor illustrated in FIGS. 7A and 7B is similar to the split-readout sensor of FIGS. 6A and 6B. However, in operation the pairs of exposure (marked "EXPOSE") and readout (marked "READ") regions in the sensor of FIGS. 7A and 7B move in opposite directions in the two sections of the sensor. For example, FIG. 7A illustrates that the pair of exposure and readout regions move toward each other in the two sections of the sensor, while FIG. 7B illustrates that the pair of exposure and readout regions move away from each other in the two sections of the sensor. This mode of operation is referred to herein as "anti-parallel" because the pairs of expose and readout regions in the sensor sections move in opposite directions.

In some embodiments, each section of the split-readout sensors depicted in FIGS. 6A, 6B, 7A, and 7B may have an associated timing diagram similar to the timing diagram illustrated in FIG. 4. Further, timing diagrams for the lower sections of the sensor in FIGS. 7A and 7B may be similar to the timing diagram illustrated in FIG. 4, but with row order "N"-to-"1" rather than "1"-to-"N" in order to account for the anti-parallel nature of the exposure/readout operations in the two sections of the sensor.

Although the illumination, exposure, and readout techniques described in the present disclosure have been cast in terms of use with a movable scan mirror that has a dead fly-back time interval, persons skilled in the art would recognize that these techniques are more broadly applicable. For example, any imaging system that is limited to less than full duty cycle image acquisition may benefit from the techniques described herein. In another example, the techniques described herein may be implemented in an imaging system that uses a rotation polygon mirror for scanning instead of a movable scan mirror.

The techniques for scanned illumination described herein are useful in imaging systems that use digital cameras operating in rolling exposure mode and rolling readout mode, that use correlated double sampling, and/or that are prevented from full duty cycle image acquisition. In an example embodiment, the techniques described herein may be implemented in an imaging system that uses one or more CMOS cameras for fluorescence-based DNA sequencing; in this embodiment, the techniques described herein contribute to overall sequencing throughput of about 100 human genome data equivalents per day.

Example Methods of Use

Figure 8:
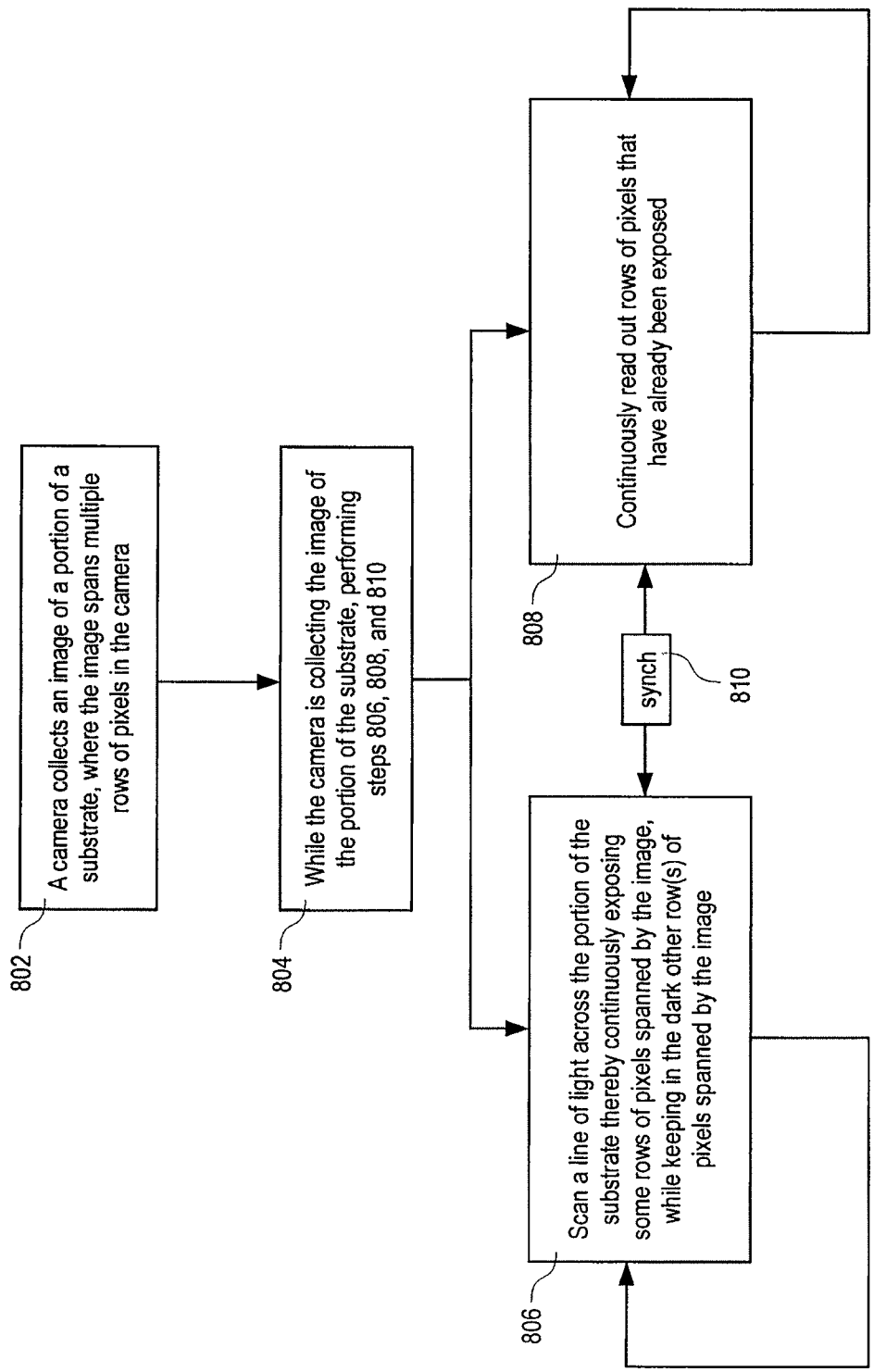
FIG. 8 is an example method for imaging a substrate using scanned illumination according to one embodiment.

FIG. 8 illustrates an example method for imaging a substrate according to one embodiment. For illustration purposes, the method in FIG. 8 is described hereinafter as being performed by a sequencing machine that includes an imaging system; it is understood, however, that the steps of the method can be performed by various different types of devices and imaging systems. Thus, the method in FIG. 8 is not limited to being performed by any particular type of machine or device, and therefore the method description hereinafter is to be regarded in an illustrative rather than a restrictive sense.

In step 802, a camera collects an image of a portion of a substrate, where the image spans multiple rows of pixels in the camera. In some embodiments, a positioning stage moves the substrate under an objective lens component in a plane that is normal to the optical axis of the objective lens component, where the substrate comprises a multitude of distinct features that are the targets of the imaging. In some aspects, the substrate comprises an array chip having target nucleic acids disposed thereon, and a sequencing machine includes an imaging system that in turn includes the camera, the positioning stage, and the objective lens component; the camera may be a CMOS camera with a line rate in a range from 1,000 lines per second to 1,000,000 lines per second, and the positioning stage may move the substrate with a velocity in a range from 100 µm/second to 1,000 mm/second. In some aspects, while the substrate is in motion, a servo mechanism changes the angle of a scan mirror such that an image of the substrate portion, acquired by the objective lens component, is kept still with respect to the camera. In some aspects, a computing device that is part of, or coupled to, the sequencing machine executes logic that controls the servo mechanism in of the scan mirror coordination with the positioning stage. For example, the logic receives feedback control information that represents the movement of the positioning stage and uses this information to adjust the input signal to the servo mechanism, which in turn changes the angle of the scan mirror thereby synchronizing the motion and/or the timing of the scan mirror with the motion and/or the timing of the positioning stage.

In step 804, while the camera is collecting the image of the portion of the substrate, the imaging system continuously and simultaneously performs (or causes to be performed) steps 806, 808, and 810. In some aspects, the camera collects a still image of the substrate portion while the substrate is being moved by a positioning stage.

In step 806, the imaging system and/or a computing device thereof scans (or causes the scan of) a line of light across the portion of the substrate being imaged, thereby continuously exposing one or more rows of pixels spanned by the image being collected while keeping in the darks other one or more rows spanned by the image. In some aspects, scanning the line of light across the substrate portion is performed in coordination with the motion of a scan mirror that keeps an image of the portion the moving substrate still with respect to the camera. For example, a computing device coupled to, or part of, the imaging system executes logic that coordinates a servo mechanism that tilts an illumination mirror (which reflects the line of light from a line generator to the scan mirror) with a servo mechanism that tilts the scan mirror, thereby synchronizing the timing of the scan mirror with the timing of the illumination mirror to cause the scanning of the line of light onto the moving substrate.

In step 808, while the scanning of the line of light proceeds across the substrate, a computing device that is part of, or coupled to, the sequencing machine executes logic that continuously reads out rows of pixels that have already being exposed and are currently not acquiring any more light. For example, the computing device executes logic that reads out the rows of exposed pixels row-by-row in rolling readout mode.

In operation, steps 806 and 808 are continuously synchronized in step 810, so that the readout operation of step 808 reads out any particular row of pixels just (or shortly) after this particular row of pixels has been exposed by the exposure operation of step 806. In this manner, extraction of image data from some rows of pixels proceeds concurrently with acquisition of another image in other (different) rows of pixels, thereby increasing the efficiency of the camera readout and therefore the overall throughput of the imaging system. For instance, in some aspects this synchronization of exposure and readout operations allows the camera to operate with readout efficiency of 55% to 90%, 90% to 95%, or even greater than 95%.

Sequencing Systems and Computing Devices

Figure 9A:
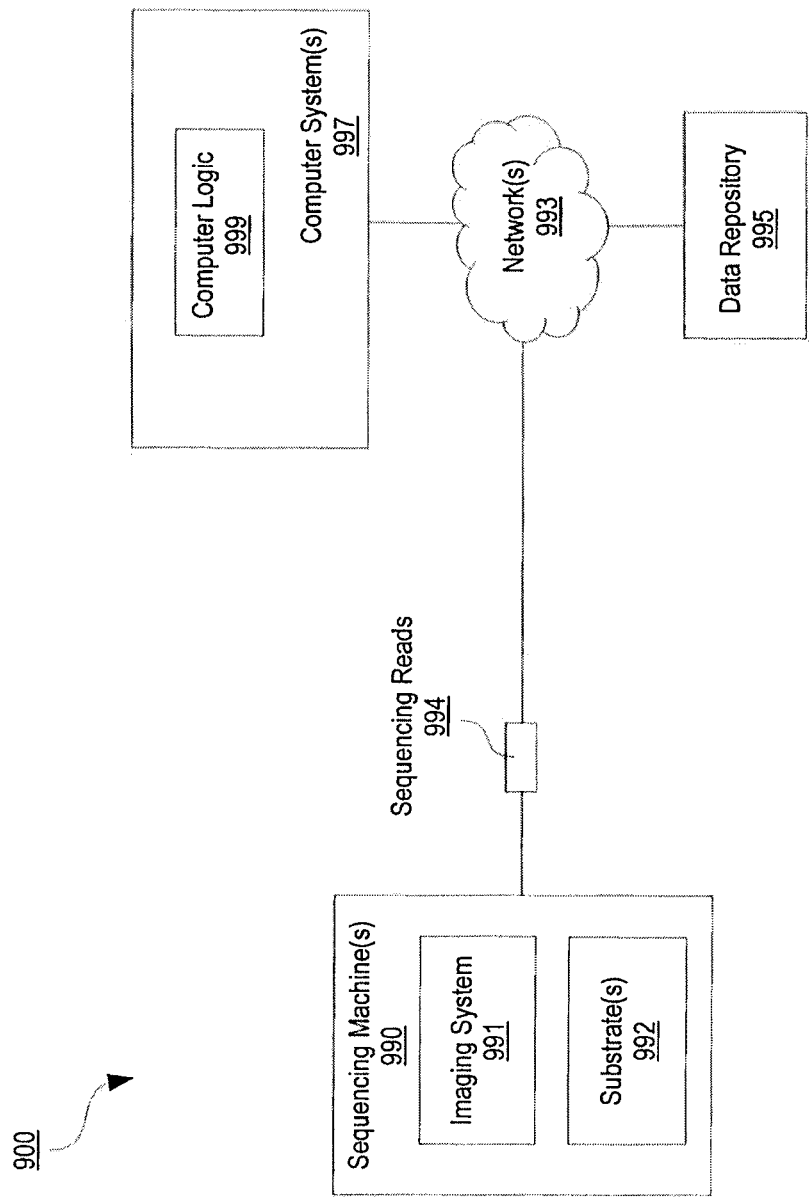
FIGS. 9A and 9B illustrate example sequencing systems.
Figure 9B:
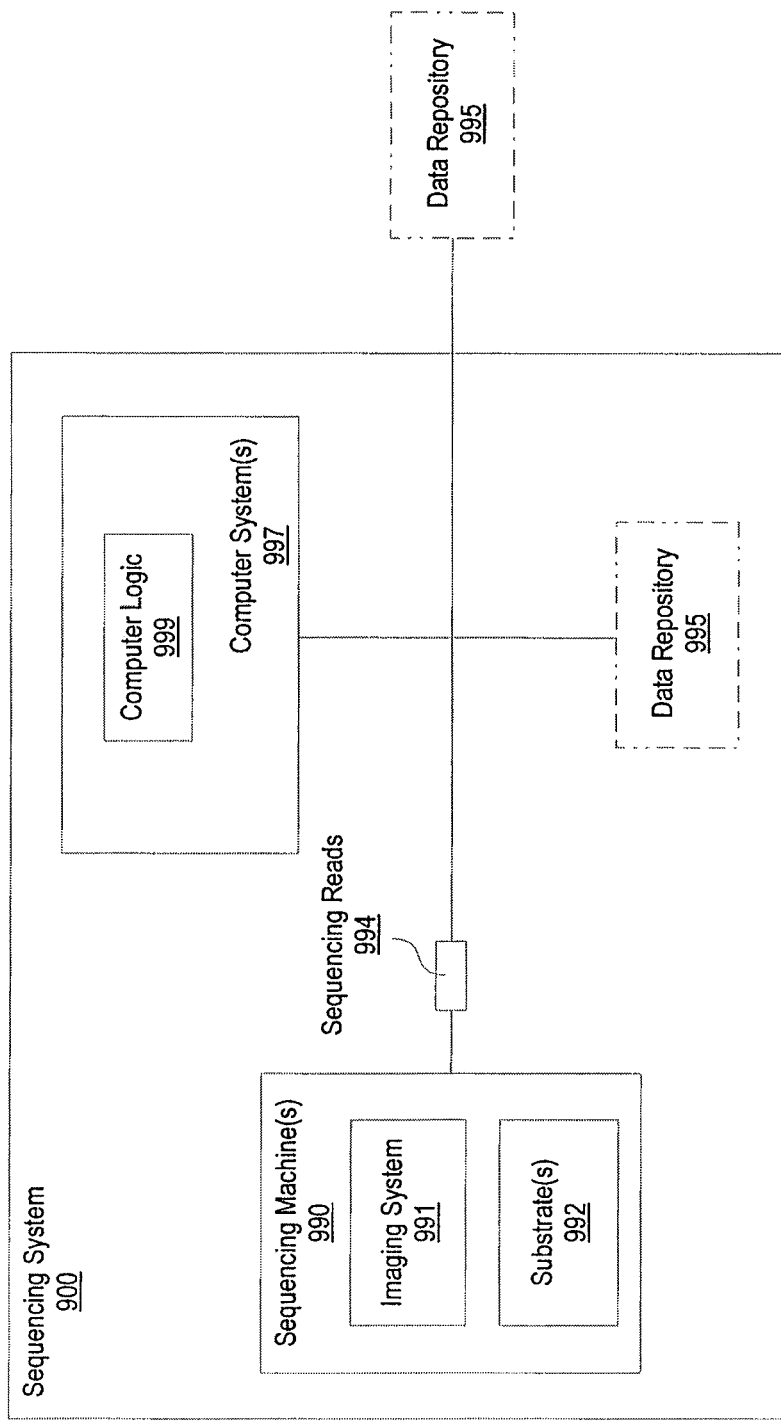

In some embodiments, sequencing of DNA samples (e.g., such as samples representing whole human genomes or samples representing exomes) may be performed by a sequencing system. FIGS. 9A and 9B illustrate example sequencing systems.

FIGS. 9A and 9B are block diagrams of example sequencing systems 900 that are configured to perform DNA sequencing according to the example embodiments described herein. A sequencing system 900 can include multiple subsystems such as, for example, one or more sequencing machines such as sequencing machine 990, one or more computer systems such as computer system 997, and one or more data repositories such as data repository 995. In the embodiment illustrated in FIG. 9A, the various subsystems of system 900 may be communicatively connected over one or more networks 993, which may include packet-switching or other types of network infrastructure devices (e.g., routers, switches, etc.) that are configured to facilitate information exchange between remote systems. In the embodiment illustrated in FIG. 9B, sequencing system 900 is a sequencing device in which the various subsystems (e.g., such as sequencing machine(s) 990, computer system(s) 997, and possibly data repository 995) are components that are communicatively and operatively coupled and integrated within the sequencing device.

In some operational contexts, data repository 995 and/or computer system(s) 997 of the embodiments illustrated in FIGS. 9A and 9B may be configured within a cloud computing environment. In a cloud computing environment, the storage devices comprising a data repository and/or the computing devices comprising a computer system may be allocated and instantiated for use as a utility and on-demand; thus, the cloud computing environment provides as services the infrastructure (e.g., physical and virtual machines, raw/block storage, firewalls, load-balancers, aggregators, networks, storage clusters, etc.), the platforms (e.g., a computing device and/or a solution stack that may include an operating system, a programming language execution environment, a database server, a web server, an application server, etc.), and the software (e.g., applications, application programming interfaces or APIs, etc.) necessary to perform any storage-related and/or computing tasks.

It is noted that in various embodiments, the techniques described herein can be performed by various systems and devices that include some or all of the above subsystems and components (e.g., such as sequencing machines, computer systems, and data repositories) in various configurations and form factors; thus, the example embodiments and configurations illustrated in FIGS. 9A and 9B are to be regarded in an illustrative rather than a restrictive sense.

A sequencing machine is configured and operable to receive one or more substrates that include target nucleic acids derived from fragments of a biological sample, and to perform sequencing on the target nucleic acids. Any suitable machine that can perform sequencing may be used, where such machine may use various sequencing techniques that include, without limitation, sequencing by hybridization, sequencing by ligation, sequencing by synthesis, single-molecule sequencing, and any other now-known or later-developed technique that is suitable for generating sequencing reads from DNA by using an imaging system as described herein. In various embodiments, a sequencing machine can sequence the target nucleic acids and can generate sequencing reads that may or may not include gaps and that may or may not be mate-pair (e.g., paired-end) reads. As illustrated in FIGS. 9A and 9B, sequencing machine 990 sequences the target nucleic acids that are on substrate(s) 992 and obtains sequencing reads 994, which are transmitted for (temporary and/or persistent) storage to data repository 995 and/or for processing by one or more computer systems 997. In accordance with the techniques described herein, sequencing machine 990 includes an imaging system 991 such as, for example, the imaging system illustrated in FIG. 1A.

Referring to FIGS. 9A and 9B, data repository 995 may be implemented on one or more storage devices (e.g., hard disk drives, optical disks, solid-state drives, etc.) that may be configured as an array of disks (e.g., such as a SCSI array), a storage cluster, or any other suitable storage organization. The storage device(s) of a data repository can be configured as internal/integral components of system 900 or as external components (e.g., such as external hard drives or disk arrays) attachable to system 900 (e.g., as illustrated in FIG. 9B), and/or may be communicatively interconnected in a suitable manner such as, for example, a grid, a storage cluster, a storage area network (SAN), and/or a network attached storage (NAS) (e.g., such as illustrated in FIG. 9A). In various embodiments and implementations, a data repository may be implemented on the storage devices as one or more file systems that store information as files, as one or more databases that store information in data records, and/or as any other suitable data storage organization.

Computer system 997 may include one or more computing devices that comprise general purpose processors (e.g., Central Processing Units, or CPUs), memory, and computer logic 999 which, along with configuration data and/or operating system (OS) software, can perform some or all of the techniques and methods described herein. For example, any of the methods involved in imaging (e.g., such as image position correction, servo rotation control, scan mirror rotation and control, illumination mirror rotation and control, chip-positioning stage movement and synchronization, feedback control, image data readout, etc.) described herein can be totally or partially performed by a computing device including a processor that can be configured to execute logic 999 for performing various steps of the methods. Further, although method steps may be presented as numbered steps, it is understood that steps of the methods described herein can be performed at the same time (e.g., by logic executing in parallel on the same computing device or in a cluster of computing devices) or in a different order. The functionalities of computer logic 999 may be implemented as a single integrated module (e.g., in an integrated logic) or may be combined in two or more software modules that may provide some additional functionalities.

In some embodiments, computer system 997 may be a single computing device. In other embodiments, computer system 997 may comprise multiple computing devices that may be communicatively and/or operatively interconnected in a grid, a cluster, or in a cloud computing environment. Such multiple computing devices may be configured in different form factors such as computing nodes, blades, or any other suitable hardware configuration. For these reasons, computer system 997 in FIGS. 9A and 9B is to be regarded in an illustrative rather than a restrictive sense.

Figure 10:
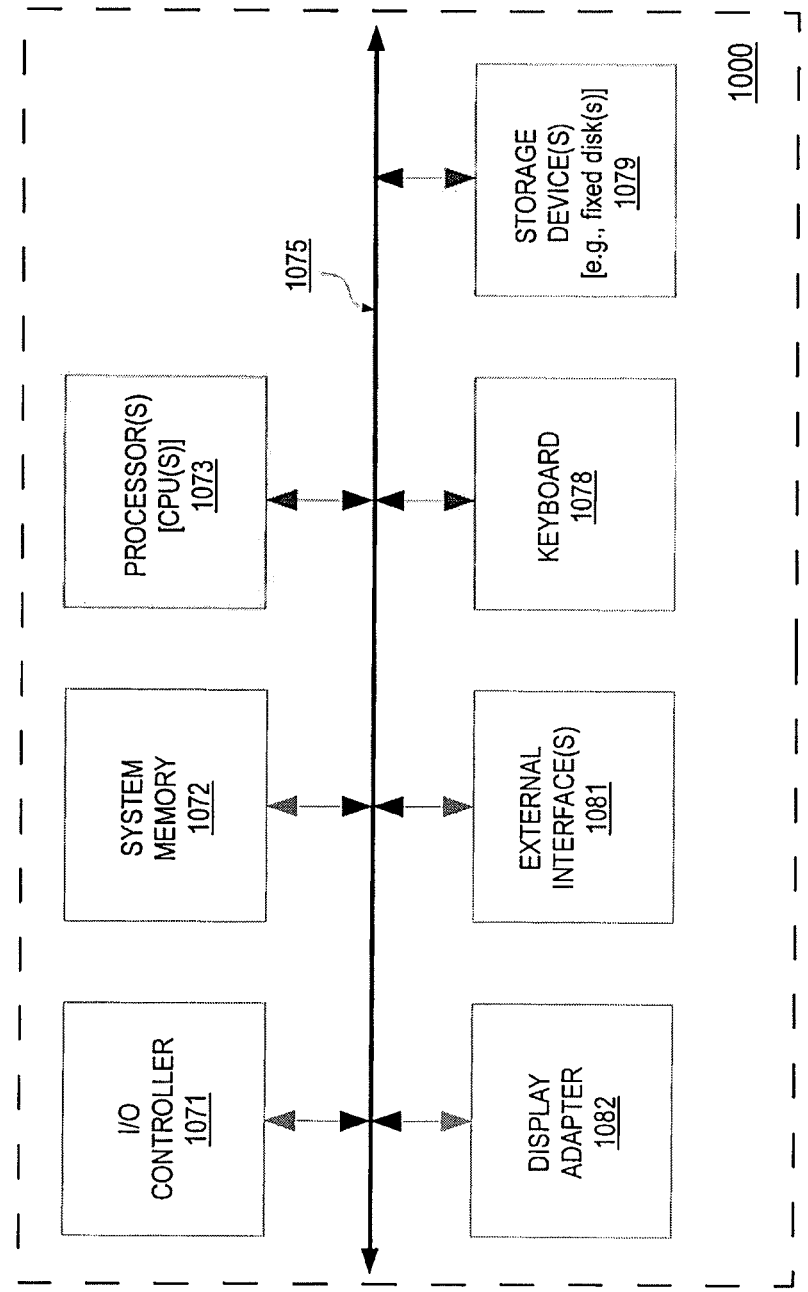
FIG. 10 illustrates an example computing device that can be used in, or in conjunction with, a sequencing machine and/or a computer system.

FIG. 10 is a block diagram of an example computing device 1000 that can be configured to execute instructions for performing various methods involved in imaging as part of sequencing machine(s) and/or computer system(s).

In FIG. 10, computing device 1000 comprises several components that are interconnected directly or indirectly via one or more system buses such as bus 1075. Such components may include, but are not limited to, keyboard 1078, persistent storage device(s) 1079 (e.g., such as fixed disks, solid-state disks, optical disks, and the like), and display adapter 1082 to which one or more display devices (e.g., such as LCD monitors, flat-panel monitors, plasma screens, and the like) can be coupled. Peripherals and input/output (I/O) devices, which couple to I/O controller 1071, can be connected to computing device 1000 by any number of means known in the art including, but not limited to, one or more serial ports, one or more parallel ports, and one or more universal serial buses (USBs). External interface(s) 1081 (which may include a network interface card and/or serial ports) can be used to connect computing device 1000 to a network (e.g., such as the Internet or a local area network (LAN)) and/or to other machines and devices. External interface(s) 1081 may also include a number of input interfaces that can receive information from various external devices. The interconnection via system bus 1075 allows one or more processors (e.g., CPUs) 1073 to communicate with each connected component and to execute (and control the execution of) instructions from system memory 1072 and/or from storage device(s) 1079, as well as the exchange of information between various components. System memory 1072 and/or storage device(s) 1079 may be embodied as one or more computer-readable non-transitory storage media that store the sequences of instructions executed by processor(s) 1073, as well as other data. Such computer-readable non-transitory storage media include, but is not limited to, random access memory (RAM), read-only memory (ROM), an electro-magnetic medium (e.g., such as a hard disk drive, solid-state drive, thumb drive, floppy disk, etc.), an optical medium such as a compact disk (CD) or digital versatile disk (DVD), flash memory, and the like. Various data values and other structured or unstructured information can be output from one component or subsystem to another component or subsystem, can be presented to a user via display adapter 1082 and a suitable display device, can be sent through external interface(s) 1081 over a network to a remote device or a remote data repository, or can be (temporarily and/or permanently) stored on storage device(s) 1079.

It should be understood that any of the methods and functionalities performed by computing device 1000 can be implemented in the form of logic using hardware and/or computer software in a modular or integrated manner. When executed, such logic is adapted to perform the various methods involved in imaging (e.g., such as image position correction, servo rotation control, scan mirror rotation and control, illumination mirror rotation and control, chip-positioning stage movement and synchronization, feedback control, image data readout, etc.) as described herein.

Sequence Determination

The imaging systems described herein may be used for a variety of biochemical analyses. One example of such analysis is sequence determination of target nucleic acids of unknown sequence. In various embodiments, a variety of sequencing methodologies may be used to determine a sequence of the nucleic acid macromolecules using the imaging systems described herein, including, but not limited to: hybridization methods (e.g., as disclosed in U.S. Pat. Nos. 6,864,052; 6,309,824; and 6,401,267); sequencing-by-synthesis methods (e.g., as disclosed in U.S. Pat. Nos. 6,210,891; 6,828,100, 6,833,246; 6,911,345; Margulies, et al. (2005), Nature 437:376-380; and Ronaghi, et al. (1996), Anal. Biochem. 242:84-89); and ligation-based methods (e.g., such as disclosed in U.S. Pat. No. 6,306,597; and Shendure et al. (2005), Science 309:1728-1739); to which reference is made for their teachings.

In some embodiments, fluorescent signals emitted from target nucleic acids disposed on a substrate (e.g., such as an array chip) are recorded by imaging them onto sensor arrays of a camera in accordance with the techniques described herein. For example, in some imaging systems, each pixel in a sensor array records the results of a separate fluorescence experiment, while in other imaging systems more than one pixel is used per experiment.

Generally, biochemical substrates allow millions of biochemical experiments to be performed in parallel. This ability accrues from the development of techniques to perform each experiment in a very small volume and to pack the experiments very close together. For example, in some embodiments a large number of attachment sites may be configured on an array chip in regular or random patterns, where the number of attachment sites may preferably be in a range from 5 billion to 50 billion, and more preferably in a range from 10 billion to 15 billion, and more generally in any sub-ranges in-between; in embodiments that use regular patterns, the pitch between the centers of any two adjacent attachment sites may be in a range from 250 nm to 1.5 μm. In operation, when macromolecules or other target nucleic acids are disposed on the attachment sites, various embodiments preferably provide single-molecule occupancy at 60% to 95% of the attachment sites; further, the yield (e.g., the average number of macromolecules or target nucleic acids that emit a signal at any given imagining run) in various embodiments may preferably be in a range from 35% to 65% of all attachment sites that hold macromolecules or target nucleic acids.

In some embodiments, DNA sequencing includes chemical processing of DNA samples, physical analysis of the processed samples to obtain raw sequence fragments, and assembly of the sequence fragments into complete genomes using computational algorithms. In some methods for DNA sequencing multiple chemical processing and physical analysis cycles may be used to build up raw sequence data before computational work begins.

In such embodiments, fluorescence imaging is used to identify DNA bases—A, C, G, or T—by designing biochemical reactions such that a different colored dye (for example, red, green, blue, or yellow) corresponds to each one. Images of such DNA experiments for each color may then be taken through an objective lens component (e.g., such as a microscope objective). The colors observed indicate the DNA bases at a particular chemical processing step.

Extracting data from such images thus depends on recording the color of fluorescence emitted by many millions or even billions of biochemical experiments that are conducted on a substrate (e.g., such as a chip).

In some embodiments, the imaging systems described herein may be used for DNA sequencing of whole human genomes such as, for example, genomes of human individuals. Commercial viability of human genome sequencing depends in part on the ability to sequence DNA rapidly and accurately. The imaging systems described herein satisfy these criteria because they support processing of large numbers of parallel DNA experiments (e.g., that are being disposed at high density on an array chip), and can facilitate rapid and accurate genomic data acquisition.

While the present invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the claims and their equivalents that issue from the present application. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. §12, ¶16.

Example Sequencing Platform

One example of DNA sequencing of human genomes is the high-accuracy, combinatorial probe-anchor ligation (cPAL) sequencing that is commercially developed by Complete Genomics, Inc. of Mountain View, Calif. The cPAL sequencing technique relies on independently assaying each base from self-assembling DNA nanoballs ("DNBs") that are loaded into patterned arrays on array chips. The first step in cPAL sequencing is loading a biochemical array chip with a random assortment of DNBs. A DNB is a concatemer that contains multiple copies, linked in a series, of the same sequence of adapters and DNA fragments that represent target nucleic acid(s); the production of such concatemers is described, for example, in U.S. patent application Ser. No. 11/451,691, which was filed on Jun. 13, 2006 by Radoje Drmanac et al., the entire content of which is hereby incorporated by reference is fully set forth herein. A set of DNBs contains DNA fragments that can collectively span an entire human genome, but when the DNBs are first attached to the attachment sites on an array chip there is no control over where any particular DNB goes. On the other hand, once the DNBs have attached to the attachment sites, they stay there for all subsequent liquid processing steps and don't move from one site to another. In subsequent processing steps various reagents and buffers are washed over the DNBs on the array chip, and fluorescent signals from the DNBs are recorded with a fluorescence imaging system.

More specifically, the cPAL sequencing technique comprises cycling of the following steps. First, an anchor is hybridized to a first adaptor in the DNBs (typically immediately at the 5' or 3' end of one of the adaptors). Enzymatic ligation reactions are then performed with the anchor to a fully degenerate probe population of, e.g., 8-mer probes, that are labeled, e.g., with fluorescent dyes. Probes may have a length, e.g., about 6-20 bases, or, preferably, about 7-12 bases. At any given cycle, the population of 8-mer probes that is used is structured such that the identity of one or more of its positions is correlated with the identity of the fluorophore attached to that 8-mer probe. For example, when 7-mer sequencing probes are employed, a set of fluorophore-labeled probes for identifying a base immediately adjacent to an adaptor may have the following structure: 3'-F1-NNNNNNAp, 3'-F2-NNNNNNGp, 3'-F3-NNNNNNCp, and 3'-F4-NNNNNNp (where "p" is a phosphate available for ligation). In yet another example, a set of fluorophore-labeled 7-mer probes for identifying a base that is three bases into a target nucleic acid from an adaptor may have the following structure: 3'-F1-NNNNANNp, 3'-F2-NNNNGNNp, 3'-F3-NNNNCNNp, and 3'-F4-NNNNTNNp. (It is to be understood that these are not genome sequences to be catalogued, but are merely examples of structure for illustrative purposes.) To the extent that the ligase discriminates for complementarity at that queried position, the fluorescent signal provides the identity of that base.

After performing the ligation and four-color imaging, the anchor 8-mer probe complexes are stripped and a new cycle is begun. With T4 DNA ligase, accurate sequence information can be obtained as far as six bases or more from the ligation junction, allowing access to at least 12 base-pairs (bp) per adaptor (six bases from both the 5' and 3' ends), for a total of 48 by per 4-adaptor DNB, 60 by per 5-adaptor DNB, and so on.

Depending on which position a given cycle is aiming to interrogate, the 8-mer probes are structured differently. Specifically, a single position within each 8-mer probe is correlated with the identity of the fluorophore with which it is labeled. Additionally, the fluorophore molecule is attached to the opposite end of the 8-mer probe relative to the end targeted to the ligation junction. For example, an anchor may be hybridized such that its 3' end is adjacent to the target nucleic acid. To query a position five bases into the target nucleic acid, a population of degenerate 8-mer probes may be used, where the probes correlate with the fifth nucleic acid from the 5' end of the 8-mer probe, which is the end of the 8-mer probe that will ligate to the anchor. The 8-mer probes are individually labeled with one of four fluorophores, where a fluorophore of Cy5 is correlated with A, Cy3 is correlated with G, Texas Red is correlated with C, and FITC is correlated with T. (While this example describes use of four fluorophores to query a single base per cycle, it should be recognized that eight or sixteen fluorophores or more may be used per cycle, increasing the number of bases that can be identified during any one cycle.)

Many different variations of cPAL or other sequencing-by-ligation approaches may be selected depending on various factors such as the volume of sequencing desired, the type of labels employed, the number of different adaptors used within each library construct, the number of bases being queried per cycle, how the DNBs are attached to the surface of the array, the desired speed of sequencing operations, signal detection approaches, and the like.

The degenerate (e.g., 8-mer) probes can be labeled in a variety of ways, including the direct or indirect attachment of radioactive moieties, fluorescent moieties, colorimetric moieties, chemiluminescent moieties, and the like. Many comprehensive reviews of methodologies for labeling DNA and constructing DNA adaptors provide guidance applicable to constructing oligonucleotide probes of the present invention. Such reviews include Kricka (2002), Ann. Clin. Biochem., 39: 114-129, and Haugland (2006); Handbook of Fluorescent Probes and Research Chemicals, 10th Ed. (Invitrogen/Molecular Probes, Inc., Eugene); Keller and Manak (1993), DNA Probes, 2nd Ed. (Stockton Press, New York, 1993); and Eckstein (1991), Ed., Oligonucleotides and Analogues: A Practical Approach (IRL Press, Oxford); and the like.

In one aspect, one or more fluorescent dyes are used as labels for the oligonucleotide probes. Labeling can also be carried out with quantum dots, as disclosed in the following U.S. patents and U.S. patent publications, incorporated herein by reference: U.S. Pat. Nos. 6,322,901; 6,576,291; 6,423,551; 6,251,303; 6,319,426; 6,426,513; 6,444,143; 5,990,479; 6,207,392; 2002/0045045; 2003/0017264; and the like. Commercially available fluorescent nucleotide analogues readily incorporated into the degenerate probes include, for example, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red, the Cy fluorophores, the Alexa Fluor® fluorophores, the BODIPY® fluorophores and the like. FRET tandem fluorophores may also be used. Other suitable labels for detection oligonucleotides may include fluorescein (FAM), digoxigenin, dinitrophenol (DNP), dansyl, biotin, bromodeoxyuridine (BrdU), hexahistidine (6xHis), phosphor-amino acids (e.g. P-tyr, P-ser, P-thr) or any other suitable label.

Image acquisition of such sequencing cycles can be performed by sequencing systems that include the imaging systems described herein. Data extraction may be performed by computing device(s) that execute(s) a series of binaries compiled from source code written in a programming language (e.g., such as C/C++), and base-calling and read-mapping may be performed by a series of Matlab and/or Perl scripts. For example, according to the example sequencing techniques described above, for each base in a target nucleic acid to be queried (e.g., for 12 bases, reading 6 bases in from both the 5' and 3' ends of each target nucleic acid portion of each DNB), a hybridization reaction, a ligation reaction, imaging, and a primer stripping reaction is performed. To determine the identity of each DNB in an array on a flow device at a given position, after performing the biological sequencing reactions, each field of view ("frame") is imaged with four different wavelengths corresponding to the four fluorescent, e.g., 8-mers used. All images from each cycle are saved in a cycle directory, where the number of images is 4× the number of frames (for example, if a four-fluorophore technique is employed). Cycle image data may then be saved into a directory structure organized for downstream processing.

Data extraction typically requires two types of image data: bright field images to demarcate the positions of all DNBs in the array; and sets of fluorescence images acquired during each sequencing cycle. A computing device executes data extraction software to identify all objects with the brightfield images, then for each such object, to compute an average fluorescence value for each sequencing cycle. For any given cycle, there are four data-points, corresponding to the four images taken at different wavelengths to query whether that base is an A, G, C, or T. These raw base-calls are consolidated, yielding a (possibly discontinuous) sequencing read for each DNB. These sequencing reads may then be matched against a reference genome by using various techniques and algorithms that can be performed on one or more computer systems that include one or more computing devices.

Selected Biochemical Definitions

Various embodiments described herein may use reagents, buffers, and other fluids that are prepared by conventional techniques involving organic chemistry, polymer technology, molecular biology (including recombinant techniques), cell biology, and biochemistry, which are within the skill of those who practice in the art. Such conventional techniques may include, without limitation, polymer array synthesis, hybridization and ligation of polynucleotides, and detection of hybridization using a label. Specific illustrations of suitable techniques can be had by reference to the examples herein. However, other equivalent procedures can, of course, also be used. Such procedures can be found in standard laboratory manuals such as Green, et al., Eds. (1999), Genome Analysis: A Laboratory Manual Series (Vols. I-IV); Weiner, Gabriel, Stephens, Eds. (2007), Genetic Variation: A Laboratory Manual; Dieffenbach, Dveksler, Eds. (2003), PCR Primer: A Laboratory Manual; Bowtell and Sambrook (2003), DNA Microarrays: A Molecular Cloning Manual; Mount (2004), Bioinformatics: Sequence and Genome Analysis; Sambrook and Russell (2006, Condensed Protocols from Molecular Cloning: A Laboratory Manual; and Sambrook and Russell (2002), Molecular Cloning: A Laboratory Manual (all from Cold Spring Harbor Laboratory Press); Stryer, L. (1995) Biochemistry (4th Ed.) W.H. Freeman, New York N.Y.; Gait, "Oligonucleotide Synthesis: A Practical Approach" 1984, IRL Press, London; Nelson and Cox (2000), Lehninger, Principles of Biochemistry 3rd Ed., W. H. Freeman Pub., New York, N.Y.; and Berg et al. (2002) Biochemistry, 5th Ed., W.H. Freeman Pub., New York, N.Y., all of which are herein incorporated in their entirety by reference for all purposes.

"Adaptor" refers to an engineered construct comprising "adaptor elements" where one or more adaptors may be interspersed within target nucleic acid in a library construct. The adaptor elements or features included in any adaptor may vary widely depending on the use of the adaptors, but typically include sites for restriction endonuclease recognition and/or cutting, sites for primer binding (e.g., for amplifying the library constructs) or anchor primer binding (e.g., for sequencing the target nucleic acids in the library constructs), nickase sites, and the like. In some aspects, adaptors are engineered so as to comprise one or more of the following: 1) a length of about 20 to about 250 nucleotides, or about 40 to about 100 oligonucleotides, or less than about 60 nucleotides, or less than about 50 nucleotides; 2) features so as to be ligated to the target nucleic acid as two "arms"; 3) different and distinct anchor binding sites at the 5' and the 3' ends of the adaptor for use in sequencing of adjacent target nucleic acid(s); and 4) one or more restriction sites.

"Amplicon" refers to the product of a polynucleotide amplification reaction. For example, an amplicon may be a population of polynucleotides that are replicated from one or more starting sequences. Amplicons may be produced by a variety of amplification reactions, including but not limited to polymerase chain reactions (PCRs), linear polymerase reactions, nucleic acid sequence-based amplification, circle dependent amplification and like reactions (see, e.g., U.S. Pat. Nos. 4,683,195; 4,965,188; 4,683,202; 4,800,159; 5,210,015; 6,174,670; 5,399,491; 6,287,824 and 5,854,033; and US Pub. No. 2006/0024711).

"Circle dependent amplification" or "CDA" refers to multiple displacement amplification of a double-stranded circular template using primers annealing to both strands of the circular template to generate products representing both strands of the template, resulting in a cascade of multiple-hybridization, primer-extension, and strand-displacement events. This leads to an exponential increase in the number of primer binding sites, with a consequent exponential increase in the amount of product generated over time. The primers used may be of a random sequence (e.g., random hexamers) or may have a specific sequence to select for amplification of a desired product. CDA results in a set of concatemeric double-stranded fragments.

"Circle dependent replication" or "CDR" refers to multiple displacement amplification of a double-stranded circular template using one or more primers annealing to the same strand of the circular template to generate products representing only one strand of the template. In CDR, no additional primer binding sites are generated and the amount of product increases only linearly with time. The primer(s) used may be of a random sequence (e.g., one or more random hexamers) or may have a specific sequence to select for amplification of a desired product. Without further modification of the end product, CDR often results in the creation of a linear construct having multiple copies of a strand of the circular template in tandem, e.g., such as a linear concatemer of multiple copies of a strand of the template.

"Complementary" or "substantially complementary" refers to the hybridization or base pairing or the formation of a duplex between nucleotides or nucleic acids, such as, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the other strand, usually at least about 90% to about 95%, and even about 98% to about 100%.

"Duplex" means at least two oligonucleotides or polynucleotides that are fully or partially complementary and which undergo Watson-Crick type base pairing among all or most of their nucleotides so that a stable complex is formed. The terms "annealing" and "hybridization" are used interchangeably to mean formation of a stable duplex. "Perfectly matched" in reference to a duplex means that the poly- or oligonucleotide strands making up the duplex form a double-stranded structure with one another such that every nucleotide in each strand undergoes Watson-Crick base pairing with a nucleotide in the other strand. A "mismatch" in a duplex between two oligonucleotides or polynucleotides means that a pair of nucleotides in the duplex fails to undergo Watson-Crick base pairing.

"Fluorophore" refers to a molecule comprising or consisting of a functional group that absorbs energy within a specific absorption spectrum and re-emits energy at a different (but equally specific) emission spectrum. Preferred fluorophores for use as markers include, but are not limited to, fluorescein, cascade blue, hexachloro-fluorescein, tetrachloro-fluorescein, TAMRA, ROX, FAM, Cy3, Cy3.5, Cy5, Cy5.5, 4,4-difluoro-5,7-diphenyl-4-bora-3a,4a-diaza-s-indacene-3-propionic acid, 4,4-difluoro-5,p-methoxyphenyl-4-bora-3a,4a-diaza-s-indacene-3-propionic acid, 4,4-difluoro-5-styryl-4-bora-3a,4-adiaz-a-S-indacene-propionic acid, 6-carboxy-X-rhodamine, N,N,N',N'-tetramethyl-6-carboxyrhodamine, Texas Red, Eosin, 4,4-difluoro-5,7-diphenyl-4-bora-3a,4a-diaza-s-indacene-3-propionic acid, 4,4-difluoro-5,p-ethoxyphenyl-4-bora-3a,4a-diaza-s-indacene-3-propionic acid and 4,4-difluoro-5-styryl-4-bora-3a,4a-diaza-S-indacene-ptopionic acid, the DyLight Fluor family available from Thermo Fisher Scientific of Waltham, Mass. and the Alexa Fluor family from Molecular Probes of Eugene, Oreg.

"Hybridization" refers to the process in which two single-stranded polynucleotides bind non-covalently to form a stable double-stranded polynucleotide. The resulting (and usually) double-stranded polynucleotide is a "hybrid" or "duplex." "Hybridization conditions" will typically include salt concentrations of less than about 1M, more typically less than about 500 mM and may be less than about 200 mM. A "hybridization buffer" is a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are usually performed under stringent conditions, e.g., conditions under which a probe will hybridize to its target subsequence but will not hybridize to the other, uncomplimentary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. Exemplary stringent conditions include a salt concentration of at least 0.01M to no more than 1M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of 30° C. are suitable for allele-specific probe hybridizations.

"Ligation" refers to the process of forming a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide. Template driven ligation reactions are described in the following references: U.S. Pat. Nos. 4,883,750; 5,476,930; 5,593,826; and 5,871,921.

"Polynucleotide", "nucleic acid", "oligonucleotide", "oligo" or grammatical equivalents used herein, refer generally to at least two nucleotides that are covalently linked together. A nucleotide is composed of a nucleobase (or just "base"), a five-carbon sugar (e.g., such as a ribose or 2'-deoxyribose), and one to three phosphate groups that form the backbone of the nucleotide. Together, the base (e.g., one of the four main nucleotide bases of C, G, A, T, and the base U found in RNA) and the sugar comprise a nucleoside. A polynucleotide generally contains phosphodiester bonds, although in some cases nucleic acid analogs may be included that have alternative backbones such as, for example: phosphoramidite, phosphorodithioate, or methylphophoroamidite linkages; and peptide nucleic acid backbones and linkages. Other analog nucleic acids include those with bicyclic structures including locked nucleic acids, positive backbones, non-ionic backbones, and non-ribose backbones.

"Primer" refers to an oligonucleotide, either natural or synthetic, which is capable, upon forming a duplex with a polynucleotide template, of acting as a point of initiation of nucleic acid synthesis and being extended from one of its ends along the template so that an extended duplex is formed. The sequence of nucleotides added during the extension process is determined by the sequence of the template polynucleotide. Primers usually are extended by a DNA polymerase.

"$T_m$" is a term commonly defined as the temperature at which half of the population of double-stranded nucleic acid molecules becomes dissociated into single strands. The equation for calculating the $T_m$ of nucleic acids is well known in the art. As indicated by standard references, a simple estimate of the $T_m$ value may be calculated by the equation: $T_m=81.5+16.6(\log 10[Na+])0.41(\%[G+C])-675/n-1.0$ m, when a nucleic acid is in aqueous solution having cation concentrations of 0.5 M, or less, the (G+C) content is between 30% and 70%, "n" is the number of bases, and "m" is the percentage of base pair mismatches (see e.g., Sambrook J et al., "Molecular Cloning, A Laboratory Manual", 3rd Edition, Cold Spring Harbor Laboratory Press (2001)). Other references include more sophisticated computations, which take structural as well as sequence characteristics into account for the calculation of Tm (see also, Anderson and Young (1985), Quantitative Filter Hybridization, Nucleic Acid Hybridization, and Allawi and SantaLucia (1997), Biochemistry 36:10581-94).

The invention has been explained with reference to specific embodiments. Other embodiments will be apparent to those of ordinary skill in the art upon reference to this description. It is therefore not intended that this invention be limited, except as indicated by the appended claims.

What is claimed is:

1. A method for operating an imaging system, the method comprising:
   collecting a two-dimensional image of a portion of a substrate on a positioning stage via a digital camera in the imaging system by moving the positioning stage in a first path of travel under an objective lens component of the imaging system that is normal to the optical axis of the objective lens component, wherein the image spans multiple rows of pixels of a sensor element in the camera;
   while the camera is collecting the image of the portion of the substrate, performing steps comprising:
      scanning a line of light across the portion of the substrate by changing an angle of a scan mirror so that the image of the portion of the substrate that is acquired by the objective lens component is kept still with respect to the digital camera while the substrate is moving in a continuous motion, thereby exposing first one or more rows of pixels spanned by the image while keeping in the dark second one or more rows of pixels spanned by the image; and
      reading out the first one or more rows of pixels while continuing to scan the line of light across the portion of the substrate thereby exposing the second one or more rows of pixels.

2. The method of claim 1 wherein changing the angle of the scan mirror is performed in coordination with scanning the line of light across the portion of the substrate.

3. The method of claim 1, wherein:
   changing the angle of the scan mirror includes a first time interval during which the line of light is scanned across the portion of the substrate and a second time interval during which the scan mirror is returned to an initial position; and
   the method further comprises ceasing to scan the line of light across the portion of the substrate during the second time interval.

4. The method of Claim 1, wherein reading out the first one or more rows of pixels is performed while the substrate is being moved in a direction that is normal to the optical axis of the objective lens component.

5. The method of claim 1, wherein scanning the line of light across the portion of the substrate comprises changing an angle of an illumination mirror to reflect light from a line generator onto the portion of the substrate.

6. The method of claim 5, wherein changing the angle of the illumination mirror is effected by a servo mechanism configured to tilt the illumination mirror.

7. The method of claim 5, further comprising:
   moving the substrate under an objective lens component of the imaging system;
   changing an angle of a scan mirror so that the image of the portion of the substrate that is acquired by the objective lens component is kept still with respect to the camera while the substrate is moving;
   wherein changing the angle of the scan mirror is performed in coordination with changing the angle of the illumination mirror.

8. The method of claim 1, further comprising keeping the first one or more rows of pixels dark between the steps of exposing the first one or more rows of pixels and reading out the first one or more rows of pixels.

9. The method of claim 1, wherein the camera comprises a split-readout sensor having at least a first section and a second section, and the steps of scanning the line of light and reading out are performed independently in each section of the split-readout sensor.

10. The method of claim 9, wherein the steps of scanning and reading out in the first section are performed in parallel to the steps of scanning and reading out in the second section.

11. The method of claim 9, wherein the steps of scanning and reading out in the first section are performed in anti-parallel to the steps of scanning and reading out in the second section.

12. The method of claim 1, wherein the line of light has a wavelength appropriate for fluorescence excitation while pixels in the camera are exposed by light having a wavelength corresponding to fluorescence emission.

13. The method of claim 1, further comprising:
   while the camera is collecting the image of the portion of the substrate, reading out the second one or more rows of pixels while continuing to scan the line of light across the substrate thereby exposing third one or more rows of pixels spanned by the image, wherein the third one or more rows of pixels are different than the second one or more rows of pixels.

14. The method of claim 13, wherein the third one or more rows of pixels are different than the first one or more rows of pixels.

15. The method of claim 1, wherein the camera is one of a CMOS camera and a non-CMOS camera operating in full-frame mode.

16. A method for operating an imaging system, the method comprising:

collecting an image of a portion of a substrate via a digital camera in the imaging system, wherein the image spans multiple rows of pixels of a sensor element in the camera;

while the camera is collecting the image of the portion of the substrate, performing steps comprising:

scanning a line of light across the portion of the substrate thereby exposing first one or more rows of pixels spanned by the image while keeping in the dark second one or more rows of pixels spanned by the image;

moving the substrate under an objective lens component of the imaging system;

changing an angle of a scan mirror so that the image of the portion of the substrate that is acquired by the objective lens component is kept still with respect to the camera while the substrate is moving; and reading out the first one or more rows of pixels while continuing to scan the line of light across the portion of the substrate, thereby exposing the second one or more rows of pixels;

wherein changing the angle of the scan mirror includes a first time interval during which the line of light is scanned across the portion of the substrate and a second time interval during which the scan mirror is returned to an initial position;

further including ceasing to scan the line of light across the portion of the substrate during the second time interval; and wherein the first time interval is greater than the second time interval.

17. The method of claim 16, wherein changing the angle of the scan mirror is performed in coordination with scanning the line of light across the portion of the substrate.

18. The method of claim 16, wherein reading out the first one or more rows of pixels is performed while the substrate is being moved in a direction that is normal to the optical axis of the objective lens component.

19. The method of claim 16, wherein scanning the line of light across the portion of the substrate comprises changing an angle of an illumination mirror to reflect light from a line generator onto the portion of the substrate.

20. The method of claim 16, further comprising keeping the first one or more rows of pixels dark between the steps of exposing the first one or more rows of pixels and reading out the first one or more rows of pixels.

21. The method of claim 16, wherein the camera comprises a split-readout sensor having at least a first section and a second section, and the steps of scanning the line of light and reading out are performed independently in each section of the split-readout sensor.

22. The method of claim 16, wherein the line of light has a wavelength appropriate for fluorescence excitation while pixels in the camera are exposed by light having a wavelength corresponding to fluorescence emission.

23. The method of claim 16, wherein the camera is one of a CMOS camera and a non-CMOS camera operating in full-frame mode.

24. An imaging system comprising:
an objective lens component; a line generator that is configured to generate a line of light that is scanned across a portion of a substrate;

a positioning stage that is configured to move the substrate in a first direction path of travel that is substantially normal to an optical axis of the objective lens component;

a digital camera that is configured to acquire a two-dimensional image of the portion of the substrate through the objective lens component; and a scan mirror that is configured to move in coordination with the positioning stage, while the line of light is being scanned across the portion of the substrate and the substrate is being moved in the first direction path of travel in a continuous motion, in order to maintain the image still with respect to the camera while the image is being acquired by the camera; and an illumination mirror and a computer logic, wherein the image spans multiple rows of pixels in the camera, and wherein while the camera is acquiring the image of the portion of the substrate: the illumination mirror is configured and operative to scan the line of light across the portion of the substrate to expose first one or more rows of pixels spanned by the image while keeping in the dark second one or more rows of pixels spanned by the image; and the computer logic is configured and operative to read out the first one or more rows of pixels while the illumination mirror continues to scan the line of light across the portion of the substrate to expose the second one or more rows of pixels.

25. The imaging system of claim 24, further comprising an illumination mirror configured to scan the line of light from the line generator onto the portion of the substrate, wherein the scan mirror is configured to move in coordination with the illumination mirror while the line of light is being scanned across the portion of the substrate and the substrate is being moved in the particular direction.

26. The imaging system of claim 25, further comprising:
a first servo mechanism configured to change an angle of the illumination mirror to scan the line of light across the portion of the substrate; and a second servo mechanism configured to change angle of the scan mirror in coordination with changes to the angle of the illumination mirror.

27. The imaging system of claim 26, wherein:
the second servo mechanism is configured to change angle of the scan mirror during a first time interval in which the line of light is scanned across the portion of the substrate;

the second servo mechanism is configured to return the scan mirror to an initial position during a second time interval in which the line of light is not scanned across the portion of the substrate, wherein the second time interval is shorter than the first time interval.

28. The imaging system of claim 24, further comprising a dichroic mirror that is configured at least to: (a) reflect the line of light from the illumination mirror onto the scan mirror in order to illuminate the portion of the substrate; and (b) pass to the camera light acquired by the objective lens component and is reflected by the scan mirror.

29. The imaging system of claim 24, wherein the camera comprises a split-readout sensor having at least two sections that can be exposed and read out independently of each other.

30. The imaging system of claim 24, wherein the camera is one of a CMOS camera and a non-CMOS camera operating in full-frame mode.

* * * * *